United States Patent
Calamai et al.

(10) Patent No.: US 12,213,975 B2
(45) Date of Patent: Feb. 4, 2025

(54) PDE9 INHIBITORS FOR TREATING SICKLE CELL DISEASE

(71) Applicant: Carduion Pharmaceuticals, Inc., Burlington, MA (US)

(72) Inventors: Edward George Calamai, Boston, MA (US); Deborah Lynn Leithead Dobbins, Boston, MA (US); Michael Paul Dehart, Boston, MA (US); James McArthur, Boston, MA (US); Shi Yin Foo, Boston, MA (US)

(73) Assignee: Carduion Pharmaceuticals, Inc., Burlington, MA (US)

( * ) Notice: Subject to any disclaimer, the term of this patent is extended or adjusted under 35 U.S.C. 154(b) by 662 days.

(21) Appl. No.: 17/186,442

(22) Filed: Feb. 26, 2021

(65) Prior Publication Data

US 2021/0177845 A1    Jun. 17, 2021

Related U.S. Application Data

(63) Continuation of application No. PCT/US2019/048898, filed on Aug. 29, 2019.

(60) Provisional application No. 62/725,725, filed on Aug. 31, 2018.

(51) Int. Cl.
| | |
|---|---|
| *A61K 31/506* | (2006.01) |
| *A61K 9/00* | (2006.01) |
| *A61K 9/20* | (2006.01) |
| *A61K 9/28* | (2006.01) |
| *A61P 7/06* | (2006.01) |

(52) U.S. Cl.
CPC .......... *A61K 31/506* (2013.01); *A61K 9/0053* (2013.01); *A61K 9/2009* (2013.01); *A61K 9/2013* (2013.01); *A61K 9/2054* (2013.01); *A61K 9/2059* (2013.01); *A61K 9/284* (2013.01); *A61P 7/06* (2018.01)

(58) Field of Classification Search
CPC .. A61K 31/506; A61K 9/0053; A61K 9/2009; A61K 9/2013; A61K 9/2054; A61K 9/2059; A61K 9/284; A61K 31/17; A61K 31/4985; A61K 9/2095; A61K 9/2866; A61K 2300/00; A61P 7/06; A61P 7/00; C07D 487/04

See application file for complete search history.

(56) References Cited

U.S. PATENT DOCUMENTS

| | | |
|---|---|---|
| 3,578,687 A | 5/1971 | Larkin et al. |
| 3,819,561 A | 6/1974 | Bruenner |
| 3,917,660 A | 11/1975 | Sasaki et al. |
| 4,599,430 A | 7/1986 | Milberger et al. |
| 5,412,137 A | 5/1995 | Prashad et al. |
| 5,716,988 A | 2/1998 | Ibrahim et al. |
| 5,741,211 A | 4/1998 | Renirie et al. |
| 5,919,816 A | 7/1999 | Hausheer et al. |
| 6,187,747 B1 | 2/2001 | Singh et al. |
| 6,262,029 B1 | 7/2001 | Press et al. |
| 6,346,231 B1 | 2/2002 | Opheim |
| 6,362,178 B1 | 3/2002 | Niewohner et al. |
| 6,376,688 B1 | 4/2002 | Ferrante et al. |
| 6,407,075 B1 | 6/2002 | Scott et al. |
| 6,410,802 B1 | 6/2002 | Dasseux et al. |
| 6,531,150 B1 | 3/2003 | Sunohara et al. |
| 6,652,879 B2 | 11/2003 | Opheim |
| 6,924,309 B2 | 8/2005 | Ferrante et al. |
| 6,998,395 B2 | 2/2006 | Jackson et al. |
| 7,312,191 B2 | 12/2007 | Rose et al. |
| 7,326,421 B2 | 2/2008 | Brekke et al. |
| 7,452,907 B2 | 11/2008 | Cheng et al. |
| 7,709,468 B2 | 5/2010 | Calderwood et al. |
| 7,741,324 B2 | 6/2010 | Crew et al. |
| 7,776,916 B2 | 8/2010 | Freeman et al. |
| 7,977,315 B2 | 7/2011 | Rose et al. |
| 8,299,080 B2 | 10/2012 | Okada et al. |
| 8,309,526 B2 | 11/2012 | Freeman et al. |
| 8,324,277 B2 | 12/2012 | Freeman |
| 8,563,565 B2 | 10/2013 | Norimine et al. |
| 8,563,609 B2 | 10/2013 | Miller |
| 8,686,038 B2 | 4/2014 | Yang |
| 8,686,167 B2 | 4/2014 | Miller |
| 8,735,449 B2 | 5/2014 | Freeman |
| 8,933,255 B2 | 1/2015 | Miller |
| 8,937,194 B2 | 1/2015 | Miller |
| 9,006,473 B2 | 4/2015 | Freeman et al. |
| 9,066,902 B2 | 6/2015 | Freeman et al. |
| 9,186,408 B2 | 11/2015 | Freeman et al. |
| 9,192,600 B2 | 11/2015 | Yang |
| 9,271,952 B2 | 3/2016 | Cushing |

(Continued)

FOREIGN PATENT DOCUMENTS

| | | |
|---|---|---|
| AU | 2011202664 B2 | 4/2012 |
| CA | 2296224 A1 | 7/2000 |

(Continued)

OTHER PUBLICATIONS

Abud-Mendoza et al., Treating severe systemic lupus erythematosus with rituximab. An open study. Reumatol. Clin. 5(4):147-152 (2009).

Adjei et al., A phase I trial of the farnesyl transferase inhibitor SCH66336: evidence for biological and clinical activity. Cancer Res. 60:1871-1877 (2000).

Akaike et al., Antagonistic action of imidazolineoxyl N-oxides against endothelium-derived relaxing factor/NO through a radical reaction. Biochem. 32:827-832 (1993).

(Continued)

*Primary Examiner* — Jessica Worsham
(74) *Attorney, Agent, or Firm* — COOLEY LLP; Matthew Pavao; Chen Chen

(57) ABSTRACT

The present disclosure relates to PDE9 inhibitors, pharmaceutical compositions comprising the PDE9 inhibitors, and methods of using the PDE9 pharmaceutical compositions for the treatment of sickle cell disease (SCD).

7 Claims, 7 Drawing Sheets

(56) References Cited

U.S. PATENT DOCUMENTS

| | | |
|---|---|---|
| 9,295,678 B2 | 3/2016 | Freeman et al. |
| 9,308,189 B2 | 4/2016 | Miller |
| 9,434,731 B2 | 9/2016 | Siegel et al. |
| 9,434,733 B2 | 9/2016 | Svenstrup et al. |
| 9,522,156 B2 | 12/2016 | Freeman et al. |
| 9,533,992 B2 | 1/2017 | Svenstrup et al. |
| 9,585,855 B2 | 3/2017 | Yang |
| 9,643,970 B2 | 5/2017 | Svenstrup et al. |
| 9,700,534 B2 | 7/2017 | Freeman et al. |
| 9,725,453 B2 | 8/2017 | Bursavich et al. |
| 9,771,366 B2 | 9/2017 | Dunn et al. |
| 9,850,249 B2 | 12/2017 | Svenstrup et al. |
| 10,513,524 B2 | 12/2019 | Svenstrup et al. |
| 2001/0037598 A1 | 11/2001 | Suppes et al. |
| 2002/0128510 A1 | 9/2002 | Durley et al. |
| 2003/0078299 A1 | 4/2003 | Ferrante et al. |
| 2004/0006248 A1 | 1/2004 | Paiocchi et al. |
| 2004/0020186 A1 | 2/2004 | Orlando et al. |
| 2004/0092590 A1 | 5/2004 | Arterburn et al. |
| 2004/0147599 A1 | 7/2004 | Gagnon et al. |
| 2004/0176451 A1 | 9/2004 | Tamai et al. |
| 2004/0220176 A1 | 11/2004 | Dickason et al. |
| 2004/0220186 A1 | 11/2004 | Bell et al. |
| 2004/0254240 A1 | 12/2004 | Ferrante et al. |
| 2005/0136103 A1 | 6/2005 | Ben-Sasson et al. |
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0099925 A1 | 5/2007 | Calderwood et al. |
| 2007/0232579 A1 | 10/2007 | Freeman et al. |
| 2007/0275893 A1 | 11/2007 | Quay |
| 2008/0096961 A1 | 4/2008 | Serhan et al. |
| 2008/0107729 A1 | 5/2008 | Amin et al. |
| 2008/0108697 A1 | 5/2008 | Ibrahim et al. |
| 2009/0030003 A1 | 1/2009 | Verhoest et al. |
| 2009/0074857 A1 | 3/2009 | Dror et al. |
| 2009/0220612 A1 | 9/2009 | Perera |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082147 A1 | 4/2011 | Harbeson et al. |
| 2011/0082206 A1 | 4/2011 | Miller |
| 2011/0092594 A1 | 4/2011 | Yang |
| 2011/0196037 A1 | 8/2011 | Yang |
| 2011/0256247 A1 | 10/2011 | Miller |
| 2011/0280852 A1 | 11/2011 | Miller |
| 2011/0312909 A1 | 12/2011 | Ciomei et al. |
| 2011/0319325 A1 | 12/2011 | Miller |
| 2012/0136034 A1 | 5/2012 | Freeman et al. |
| 2012/0157458 A1 | 6/2012 | Ripka et al. |
| 2012/0295925 A1 | 11/2012 | Tung et al. |
| 2013/0005730 A1 | 1/2013 | Sun et al. |
| 2013/0039956 A1 | 2/2013 | Dietz |
| 2013/0059912 A1 | 3/2013 | Freeman |
| 2013/0101514 A1 | 4/2013 | Cushing |
| 2013/0143907 A1 | 6/2013 | Norimine et al. |
| 2013/0210917 A1 | 8/2013 | Freeman et al. |
| 2014/0024713 A1 | 1/2014 | Yang |
| 2014/0088081 A1 | 3/2014 | Claffey et al. |
| 2014/0243380 A1 | 8/2014 | Yang |
| 2014/0271844 A1 | 9/2014 | Miller |
| 2014/0308336 A1 | 10/2014 | Indolfi et al. |
| 2015/0018417 A1 | 1/2015 | Freeman et al. |
| 2015/0045348 A1 | 2/2015 | Svenstrup et al. |
| 2015/0051283 A1 | 2/2015 | Batthyany Dighiero et al. |
| 2015/0246059 A1 | 9/2015 | Freeman et al. |
| 2015/0274736 A1 | 10/2015 | Svenstrup et al. |
| 2016/0081961 A1 | 3/2016 | Cushing |
| 2016/0081962 A1 | 3/2016 | Miller et al. |
| 2016/0151318 A1 | 6/2016 | Yang |
| 2017/0081333 A1 | 3/2017 | Svenstrup et al. |
| 2017/0095437 A1 | 4/2017 | Jorkasky |
| 2017/0173018 A1 | 6/2017 | Svenstrup et al. |
| 2018/0092948 A1 | 4/2018 | Weiss et al. |
| 2018/0194770 A1 | 7/2018 | Svenstrup et al. |
| 2020/0247750 A1 | 8/2020 | Nam et al. |
| 2021/0085684 A1 | 3/2021 | Svenstrup et al. |
| 2021/0094960 A1 | 4/2021 | Svenstrup et al. |
| 2021/0107911 A1 | 4/2021 | Buttar et al. |

FOREIGN PATENT DOCUMENTS

| | | |
|---|---|---|
| CN | 1344268 A | 4/2002 |
| CN | 101448829 A | 6/2009 |
| CN | 101557826 A | 10/2009 |
| CN | 101687876 A | 3/2010 |
| CN | 102099024 A | 6/2011 |
| CN | 102307464 A | 1/2012 |
| CN | 101687876 B | 12/2012 |
| CN | 103313988 A | 9/2013 |
| CN | 104093720 A | 10/2014 |
| CN | 104220060 A | 12/2014 |
| CN | 103313988 B | 6/2016 |
| CN | 107810187 A | 3/2018 |
| DE | 102012008730 A1 | 6/2013 |
| EP | 0911333 A1 | 4/1999 |
| EP | 1097706 A1 | 5/2001 |
| EP | 1407767 A1 | 4/2004 |
| EP | 1772149 A1 | 4/2007 |
| EP | 2123301 A1 | 11/2009 |
| EP | 2123801 A1 | 11/2009 |
| GB | 587992 A | 5/1947 |
| GB | 1407932 A | 10/1975 |
| JP | S62132804 A | 6/1987 |
| JP | 2001520189 A | 10/2001 |
| JP | 2003509485 A | 3/2003 |
| JP | 2004509097 A | 3/2004 |
| JP | 2008520739 A | 6/2008 |
| JP | 2011525525 A | 9/2011 |
| JP | 2018123119 A | 8/2018 |
| WO | WO-9809621 A1 | 3/1998 |
| WO | WO-9924433 A1 | 5/1999 |
| WO | WO-0106983 A2 | 2/2001 |
| WO | WO-0121575 A1 | 3/2001 |
| WO | WO-0160778 A2 | 8/2001 |
| WO | WO-0178654 A2 | 10/2001 |
| WO | WO-0178719 A1 | 10/2001 |
| WO | WO-0179156 A1 | 10/2001 |
| WO | WO-0115673 A3 | 3/2002 |
| WO | WO-0222559 A2 | 3/2002 |
| WO | WO-02102364 A1 | 12/2002 |
| WO | WO-03031399 A1 | 4/2003 |
| WO | WO-03037432 A1 | 5/2003 |
| WO | WO-03037899 A1 | 5/2003 |
| WO | WO-03039533 A1 | 5/2003 |
| WO | WO-03093270 A1 | 11/2003 |
| WO | WO-2004096811 A1 | 11/2004 |
| WO | WO-2005041972 A1 | 5/2005 |
| WO | WO-2005073164 A1 | 8/2005 |
| WO | WO-2005110396 A2 | 11/2005 |
| WO | WO-2006055965 A2 | 5/2006 |
| WO | WO-2006086727 A2 | 8/2006 |
| WO | WO-2007137819 A1 | 12/2007 |
| WO | WO-2007140433 A2 | 12/2007 |
| WO | WO-2008008767 A2 | 1/2008 |
| WO | WO-2008011085 A1 | 1/2008 |
| WO | WO-2008103753 A2 | 8/2008 |
| WO | WO-2008139293 A1 | 11/2008 |
| WO | WO-2009017802 A1 | 2/2009 |
| WO | WO-2009038671 A2 | 3/2009 |
| WO | WO-2009129495 A1 | 10/2009 |
| WO | WO-2009134383 A2 | 11/2009 |
| WO | WO-2009149496 A1 | 12/2009 |
| WO | WO-2009155439 A2 | 12/2009 |
| WO | WO-2010012777 A1 | 2/2010 |
| WO | WO-2010042877 A1 | 4/2010 |
| WO | WO-2010078504 A1 | 7/2010 |
| WO | WO-2010084438 A1 | 7/2010 |

(56) References Cited

FOREIGN PATENT DOCUMENTS

| WO | WO-2010129763 A1 | 11/2010 |
|---|---|---|
| WO | WO-2010129777 A1 | 11/2010 |
| WO | WO-2011011882 A1 | 2/2011 |
| WO | WO-2011014261 A1 | 2/2011 |
| WO | WO-2011028820 A1 | 3/2011 |
| WO | WO-2011030351 A2 | 3/2011 |
| WO | WO-2011041639 A2 | 4/2011 |
| WO | WO-2011056126 A1 | 5/2011 |
| WO | WO-2011098746 A1 | 8/2011 |
| WO | WO-2012040230 A1 | 3/2012 |
| WO | WO-2012110441 A1 | 8/2012 |
| WO | WO-2013053690 A1 | 4/2013 |
| WO | WO-2013110768 A1 | 8/2013 |
| WO | WO-2013116765 A1 | 8/2013 |
| WO | WO-2013170069 A1 | 11/2013 |
| WO | WO-2014036555 A1 | 3/2014 |
| WO | WO-2015023557 A1 | 2/2015 |
| WO | WO-2015073527 A1 | 5/2015 |
| WO | WO-2015185499 A1 | 12/2015 |
| WO | WO-2017005786 A1 | 1/2017 |
| WO | WO-2018009424 A1 | 1/2018 |
| WO | WO-2018218104 A1 | 11/2018 |
| WO | WO-2019226944 A1 | 11/2019 |
| WO | WO-2020047311 A1 | 3/2020 |
| WO | WO-2020206336 A1 | 10/2020 |
| WO | WO-2020227399 A1 | 11/2020 |

OTHER PUBLICATIONS

Akinsheye et al., Fetal hemoglobin in sickle cell anemia. Blood 118(1):19-27 (2011).
Alber, Signaling mechanisms of the *Mycobacterium tuberculosis* receptor Ser/Tur protein kinases. Curr. Opin. Struct. Biol. 19(6):650-657 (2009).
Almeida et al., High expression of the cGMP-specific phosphodiesterase, PDE9A, in sickle cell disease (SCD) and the effects of its inhibition in erythroid cells and SCD neutrophils. British Journal of Haematology 142(5):836-44 (2008).
Almeida et al.: Hydroxyurea and a cGMP-amplifying agent have immediate benefits on acute vaso-occlusive events in sickle cell disease mice. Blood. 120(14):2879-2888 (2012).
Alsultan et al., Genetic studies of fetal hemoglobin in the Arab-Indian haplotype sickle cell-β(0) thalassemia. American Journal of Hematology 88(6):531-532 (2013).
Altschul et al., Gapped BLAST and PSI-BLAST: a new generation of protein database search programs. Nucleic Acids Res. 25(17) 3389-3402 (1997).
Anand et al., Synthesis and evaluation of small libraries of triazolylmethoxy chalcones, flavanones and 2-aminopyrimidines as inhibitors of mycobacterial FAS-II and PknG. Biorganic & Medicinal Chem. 20(17):5150-5183 (2012).
Arbeeny, C. et al., Renoprotection by treatment with CXA-10, an Endogenous Nitro Fatty Acid. Poster, Nov. 5, 2015, 1 page (2015).
Arbeeny, C. et al., Renoprotection by treatment with CXA10, an endogenous nitro-fatty Acid. J. Am. Soc. Nephrol. 26:126A, Abstract THP0158 (2015).
Arnold et al., Nitric oxide activates guanylate cyclase and increases guanosine 3':5'-cyclic monophosphate levels in various tissue preparations. Proc. Natl. Acad. Sci. 74:3203-3207 (1977).
Artim et al., Nitro-oleic acid targets transient receptor potential (TRP) channels in capsaicin sensitive afferent nerves of rat urinary bladder. Expt. Neural. 232:90-99 (2011).
Asakura et al., Synthesis and biological evaluation of y-fluoro-,y-unsaturated acids. J of Flourine Chem. 127:800-808 (2006).
Aunapuu et al., Morphological changes in experimental postischemic rat kidney. A pilot study. Ann. Anat. 187(1):63-70 (2005).
Baker et al., Convergence of nitric oxide and lipid signaling: Anti-inflammatory nitro-fatty acids. Free Radic. Biol. Med. 46:989-1003. (2009).

Baker et al., Fatty acid transduction of nitric oxide Signaling. J Biol. Chem. 280(51):42464-42475 (2005).
Baker et al., Nitro-fatty acid reaction with glutathione and cysteine; kinetic analysis of thiol alkylation by a Michael addition reaction. J of Biol. Chem. 282(42):31085-31093 (2007).
Baker et al., Red cell membrane and plasma linoleic acid nitration products: Synthesis, clinical identification, and quantitation. Proc. Natl. Acad. Sci. 101(32):11577-11582 (2004).
Balazy et al., Vicinal nitrohydroxyeicosatrienoic acids: vasodilator lipids formed by reaction of nitrogen dioxide with arachidonic acid. J Pharmacol. Ex Ther. 299(2):611-619 (2001).
Balazy, Isomerization and Nitration of arachidonic acid by nitrogen dioxide. Advances in Mass Spectrometry 15:375-376 (2001).
Baldus et al., Endothelial transcytosis of myeloperoxidase confers specificity to vascular ECM proteins as targets of tyrosine nitration. J Clin. Invest. 108(12):1759-1770 (2001).
Baldus et al., Is NO news bad news in acute respiratory distress syndrome. Am. J Respir. Crit. Care Med. 163:308-310 (2001).
Ballini et al., Fast diastereoselective Baylis-Hillman reaction by nitroalkenes: synthesis of di- and triene derivatives. Tetrahedron 60:4995-4999 (2004).
Ballini et al., Nitroalkanes and ethyl glyoxalate as common precursors for the preparation of both 13 keto esters and a, 13-unsaturated esters. Tetrahedron Letters 45:7027-7029 (2004).
Ballini et al., (Z)-7-nitro-3-heptene as central intermediate for the synthesis of jasmone, methyl jasmonate and y-jasmolactone. Synthetic Communications 19(3-4):575-583 (1989).
Banker et al., Modern Pharmaceutics, Marcel Dekker, Inc. 1979, New York (TOC) (1979).
Bates et al., Nitroalkene fatty acids mediate activation of Nrf2/ARE-dependent and PPARy-dependent transcription by distinct signaling pathways and with significantly different potencies. Biochem. 50:7765-7773 (2011).
Bates et al., Noncatalytic interactions between glutathione s-transferases and nitroalkene fatty acids modulate nitroalkene-mediated activation of peroxisomal proliferator-activated receptory. Biochem. 48:4159-4169 (2009).
Batthyany et al., Reversible post-translational modification of proteins by nitrated fatty acids in vivo. J Biol. Chem. 281(29):20450-20463 (2006).
Baumer Iodostarin 'Roche' in the treatment of syphilis. Deutsche Medizinische Wochenschrifr 39:1361 (case abstract) (1 page) (1913).
Beckman et al., Apparent hydroxyl radical production by peroxynitrite: implications for endothelial injury from nitric oxide and superoxide. Proc. Natl. Acad. Sci. 87:1620-1624 (1990).
Bell-Parikh et al., Biosynthesis of 15-deoxy-A12 14-PGJ2 and the ligation of PPARy. J Clin. Invest. 112(6):945-955 (2003).
Bennett et al., Cecil Textbook of Medicine 1996, 20th Ed., 1, 1004-1010 (1996).
Berge, S.M. et al., (1977) "Pharmaceuticals Salts", J. Pharma. Sci. 66: 1-19.
Bervejillo et al., Estudio del potencial anti-aterogenico del AANO2 in vivo. Tesina del grado de la Licenciatura en Bioquiica, Facultad de Ciencias, UdeIR Feb. 2012, 5-6, Fig. 2 (in Spanish with English summary) (2012).
Biegert et al., Sequence context-specific profiles for homology searching. PNAS 106(10):3770-3775. (2009).
Bjorn, Clues emerge about benefits of briefly blocking blood flow. Nature 15(2):132 (2009).
Blair et al., Bathophenanthrolinedisulphonic acid and bathocuproinedisulphonic acid, water soluble reagents for iron and copper. Talanta 7(3-4):163-174 (abstract) (1961).
Blakemore, The modified Julia olefination: alkene synthesis via the condensation of metallated heteroarylalkylsulfones with carbonyl compounds. J Chem. Soc. Perkin Trans. I. 23:2563-2585 (2002).
Blanco et al., 6-Methylnitroarachidonate: A novel esterified nitroalkene that potently inhibits platelet aggregation and exerts cGMP-mediated vascular relaxation. Free Radic. Biol. Med. 50:411-418 (2011).
Bligh et al., A rapid method of total lipid extraction and purification. Can. J Biochem. Physiol. 37(8):911-917 (1959).
Blockland, A. et al., (2006) "Improving Memory: A Role for Phosphodiesterases", Curr. Pharm. Des. 12(20):2511-2523.

(56) References Cited

OTHER PUBLICATIONS

Bloodsworth et al., Nitric oxide regulation of free radical- and enzyme-medicated lipid and lipoprotein oxidation. Arterioscler Thromb. Vasc. Biol. 20:1707-1715 (2000).
Boden et al., Free fatty acids in obesity and type 2 diabetes: defining their role in the development of insulin resistance and -cell dysfunction. Euro. J Clin. Invest. 32(Suppl. 3):14-23 (2002).
Bonacci et al., Electrophilic fatty acids regulate matrix metalloproteinase activity and expression. J Biolo. Chem. 286(18):16074-16081 (abstract) (2011).
Bonacci et al., Gas-phase fragmentation analysis of nitro-fatty acids. J Am. Soc. Mass Spec. 22:1534-1551 (2011).
Bonacci et al., Nitro-oleic acid improves insulin signaling via protein tyrosine phosphatase-Ib inhibition. Free Radical Bio. Med. Elsevier Science, 45(Suppl. 1):SI54 (abstract) (2008).
Bonomi et al., Direct metal ion substitution at the [M(Scys)4] 2 site of rubredoxin. J Biol. Inorg. Chem. 3(6):595-605 (1998).
Borniquel et al., Nitrated oleic acid up-regulates PPARγ and attenuates experimental inflammatory bowel disease. Free Radic. Bio. Med. 49(4):499-505 (2010).
Boruwa et al., Catalytic asymmetric henry reaction. Tetrahedron: Asymmetry Report No. 90(17):3315-3326 (2006).
Breer, H. et al., (1990) "Rapid Kinetics of Second Messenger Formation in Olfactory Transduction" Nature 345 :6270):65-68.
Burdge, a-Linolenic acid metabolism in men and women: nutritional and biological ilmplications. Clin. Nutri. Metabol. Care 7:137-144 (2004).
Cannon, Burger's Medicinal Chemistry and Drug Discovery 1995, Fifth Edition, I: Principles and Practice, Chap. 19, John Wiley & Sons, Inc., 783-802 (1995).
Castro et al., Cytochrome c: a catalyst and target of nitrate-hydrogen peroxide-dependent protein nitration. Arch. Biochem. Biophys. 421:99-107 (2004).
Chawla, et al. Current Research & Information on Pharmaceutical Sciences (CRIPS), 5(1), 2004, 9-12.
Chawla et al., PPAR-y dependent and independent effects on macrophage-gene expression in lipid metabolism and inflammation. Nat. Med. 7(1):48-52 (2001).
Chen et al., Peroxisome proliferator-activated receptors and the cardiovascular system. Vitam. Harm. 66:157-188 (2003).
Chen et al., Synthesis and screening of novel vitamin E derivatives for anticancer functions. European J of Medicinal Chem. 58:72-83 (2012).
Chen et al., Troglitazone inhibits atherhosclerosis in apolipoprotein E-knockout mice: pleiotropic effects on CD36 expression and HDL. Arterioscler Thromb. Vasc. Biol. 21:372-377 (2001).
Chieffo, C. et al., Use of an obese population in phase I to evaluate the pharmacology of oral CXA-10, an endogenous nitro-fatty acid signaling agent. Poster, 4 pages (Sep. 26, 2016).
Christiansen, T. et al., Monocyte chemoattractant protein-1 is produced in isolated adipocytes, associated with adiposity and reduced after weight loss in morbid obese subjects. International Journal of Obesity 29:146-150 (2005).
Ückert [Ueckert] et al., Phosphodiesterase inhibitors in clinical urology. Expert Review in Clinical Pharmacology 6(3):323-332 (2013).
Ückert [Ueckert], S. et al., "Phosphodiesterase (PDE) inhibitors in the treatment of lower urinary tract dysfunction" (2011) Br. J. Clin. Pharmacol 72(2): 197-204.
Clapp et al., Oxygenation of monounsaturated fatty acids by soybean liposygenase-1: evidence for transient hydroperoxide formation. Biochem. 45:15884-15892 (2006).
Claudel et al., Reduction of atherosclerosis in apolipoprotein E knockout mice by activation of the retinoid X receptor. Proc. Natl. Acad. Sci. 98(5):2610-2615 (2001).
Coffey et al., Catalytic consumption of nitric oxide by 12/15-lipoxygenase: Inhibition of monocyte soluble guanylate cyclase activation. Proc. Natl. Acad. Sci. 98(14):8006-8011 (2001).
Cole et al., Deciphering the biology of *Mycobacterium tuberculosis* from the complete genome sequence. Nature 393:537-544 (1998).

Cole et al., Nitro-fatty acid inhibition of neointima formation after endoluminal vessel injury. Circ. Res. Nov. 6, 2009, 1-8; Suppl. Materials 1-6. (2009).
Coles et al., Nitrolinoleate inhibits platelet activation by attenuating calcium mobilization and inducing phosphorylation of vasodilator-stimulated phosphoprotein through elevation of cAMP. J Biol. Chem. 277(8):5832-5840 (2002).
Coles et al., Nitrolinoleate inhibits superoxide generation, degranulation, and integrin expression by human neutrophils. Novel antiinflammatory properties of nitric oxide-derived reactive species in vascular cells. Circ. Res. 91:375-381 (2002).
Collins et al., Troglitazone inhibits formation of early atherosclerotic lesions in diabetic and nondiabetic low density lipoprotein receptor-deficient mice. Arterioscler Thromb. Vasc. Biol. 21:365-371 (2001).
Conran, N. "Prospects for early investigational therapies for sickle cell disease" (2015) Expert Opin. Investig. Drugs 24(5):595-602.
Cooke, S.F. et al., (2006) "Plasticity in the Human Central Nervous System" Brain 129(7):1659-1673.
Cosby et al., Nitrite reduction to nitric oxide by deoxyhemoglobin vasodilates the human circulation. Nat. Med. 9(12):1498-1505 (2003).
Cowley et al., The *Mycobacterium tuberculosis* protein serine/threonine kinase PknG is linked to cellular glutamate/glutamine levels and is important for growth in vivo. Molecular Microbio. 52(6):1691-1702 (2004).
Cui et al., Nitrated fatty acids: endogenous anti-inflammatory signaling mediators. J Biol. Chem. 281(47):35686-35698 (2006).
Da Silva et al., Phosphodiesterase-9 (PDE9) inhibition with BAY 73-6691 increases corpus cavernosum relaxations mediated by nitric oxide-cyclic GMP pathway in mice. International Journal of Impotence Research 25(2):69-73 (2013).
Dang et al. (Hung), Anti-inflammatory constituents of the red alga gracilaria verrucosa and their synthetic analogues. J Nat. Prod. 71(2):232-240 (2008).
Dangi et al., Biogenic synthesis, purification, and chemical characterization of anti-inflammatory resolvins derived from docosapentaenoic acid (DPAn-6). J Biol. Chem. 284(22):14744-14759 (2009).
Davies et al., Oxidized alkyl phospholipids are specific, high affinity peroxisome proliferator-activated receptor y ligands and agonists. J Biol. Chem. 276(19):16015-16023 (2001).
De Meijere et al., Metal-catalyzed cross-coupling reactions. VViley-VCH Verlag GMbH & Co. 2004, Weinheim, vols. 1 and 2, XXII, ISBN-10: 3-527-30518-1 and ISBN-13: 978-3-527-30518-6 (TOC) (2004).
Defronzo et al., Insulin resistance: a multifaceted syndrome responsible for NIDDM, obesity, hypertension, dyslipidemia, and atherosclerotic cardiovascular disease. Diabetes Care 14(3):175-194 (1991).
Del Mar Grasa et al., Daily oral oleoyl-estrone gavage induces a dose-dependent loss of fat in Wistar rats. Obesity Res. 9(3):202-209 (2001).
Delerive et al., Oxidized phospholipids activated PPARa in a phospholipase A2-dependent manner. FEES Lett. 471:34-38 (2000).
Dembitsky et al., Natural halogenated fatty acids: their analogues and derivatives. Progress in Lipid Research 41(4):315-367 (2002).
Denicola et al., Diffusion of nitric oxide into low density lipoprotein. J Biol. Chem. 277(2):932-936 (2002).
Denicola et al., Diffusion of peroxynitrite across erythrocyte membranes. Proc. Natl. Acad. Sci. 95:3566-3571 (1998).
Desper et al., Getting a tree fast: neighbor joining, FastME, and distance-based methods. Curr. Protoc. Bioinformatics, Chap. 6, Unit 6.3 (2006).
Diabetic ketoacidosis in www.mayoclinic.org/diseases-conditions/diabetic-ketoacidosis/basics/treatment/con-20026470 (retrieved from the internet Jan. 21, 2016).
D'Ischia et al., Medium-dependent competitive pathways in the reactions of polyunsaturated fatty acids with nitric oxide in the presence of oxygen. Structural characterisation of nitration products and a theoretical insight. Tetrahedron 55:9297-9308 (1999).
D'Ischia, Oxygen-dependent nitration of ethyl linoleate with nitric oxide. Tetrahedron Lett. 37(32):5773-5774 (1996).

(56) References Cited

OTHER PUBLICATIONS

Dodge et al., Composition of phospholipids and of phospholipids fatty acids and aldehydes in human red cells. J Lipid Res. 8:667-675 (1967).
Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.
Dorwald, Side Reactions in Organic Synthesis. Wiley-VCH, 1-16 (2005).
Duan et al., Nephrotoxicity of high- and low-osmolar contrast media: Protective role of forsinopril or telmisartan in a rat model. J Central S. Univ. 32(5):812-818 (2007).
Duncton, M.A.J. et al. (2008) "Preparation of Aryloxetanes and Arylazetidines by Use of an Alkyl-Aryl Suzuki Coupling" Organic Letters 10(15):3259-3262.
Eardley, K.S. et al., The relationship between albuminuria, MCP-1/CCL2, and interstitial macrophages in chronic kidney disease. Kidney Int. 69:1189-1197 (2006).
Easton et al., Polyunsaturated nitroalkanes and nitro-substituted fatty acides. Synthesis 3:451-457 (2001).
Eberhardt et al., Prevalence of overweight and obesity among adults with Diagnosed Diabetes—United States, 1988-1994 and 1999-2002. CDC, Nov. 19, 2004; 53(45):1066-1068 (2004).
Eiserich et al., Myeloperoxidase, a leukocyte-derived vascular NO oxidase. Sci. 296:2391-2394 (2002).
Eiserich et al., Pathophysiology of nitric oxide and related species: free radical reactions and modification of biomolecules. Malec. Aspects Med. 19:221-357 (1998).
Escudier et al., Bevacizumab plus interferon alfa-2a for treatment of metastatic renal cell carcinoma: a randomized, double-blind phase III trial. The Lancet 370:2103-2111 (2007).
Eurasian Patent Application No. 202190460 Office Action received Jul. 16, 2021.
Evans et al., PPARs and the complex journey to obesity. Nat. Med. 10(4):1-7 (2004).
Ex Parte Sauerberg, Appeal 2015-007064, Decided Jan. 12, 2017.
Extended European Search Report dated Oct. 25, 2016 in Application No. 16185105.0, entitled PDE9I With Imidazo Pyrazinone Backbone.
Extended European Search Report issued Mar. 10, 2017 in European Application No. 17152165.1, entitled "PDE9I With Imidazo Triazinone Backbone".
Fazzari, M. et al., Generation and esterification of electrophilic fatty acid nitroalkenes in triacylglycerides. Free Radical Biology and Medicine 87:113-124 (2015).
Feelisch et al., Concomitant S-, N-, and heme-nitros(yl)ation in biological tissues and fluids: implications for the fate of NO in vivo. FASEB J 16:1775-1785 (2002).
Ferreira et al., Macrophage activation induces formation of the anti-inflammatory lipid cholesteryl-nitrolinoleate. Biochem. J. 417:223-234 (2009).
Ferry et al., Binding of prostaglandins to human PPARγ: tool assessment and new natural ligands. Eur. J Pharmacol. 417:77-89 (2001).
Final Office Action for U.S. Appl. No. 14/962,170, Nov. 1, 2017, 8 Pages.
Finlayson-Pitts et al., A Fourier transform infrared spectrometry study of the reactions of phosphatidylcholines with gaseous N2 O5 and NO2. Toxicol. Appl. Pharmacol. 89:438-448 (1987).
Fisher, D.A. et al., (1998) "Isolation and Characterization of PDE9A, a Novel Human cGMP-specific Phosphodiesterase" J_Boil_Chem_ 273(25):15559-15564.
Fiuza et al., From the characterization of the four serine/threonine protein kinases (PknA/B/G/L) of corynebacterium glutamicum toward the role of PknA and PknB in cell division. J Biol. Chem. 283(26):18099-18112 (2008).
Forman et al., 15-Deoxy-A 12 14-prostaglandin J2 is a ligand for the adipocyte determination factory PPAR gamma. Cell 83:803-812 (1995).
Freeman et al., Nitro-fatty acid formation and signaling. J of Biol. Chem. 283(23):15515-15519 (2008).
Freshney, Culture of Animal Cells. A Manual a/Basic Technique 1983, Alan R. Liss, Inc., New York, 1-6 (1983).
Fu et al., Oleylethanolamide regulates feeding and body weight through activation of the nuclear receptor PPAR-a. Nature 425:90-93 (2003).
Furstner et al., Total synthesis of epohelmin b and its analogues. Chem. Asian J 3:310-318 (2008).
Galle et al., Pulmonary hypertension and pulmonary arterial hypertension: a clarification is needed. Eur Respir J. 36(5):986-990 (2010).
Gallon et al., The identification of the allylic nitrite and nitro derivatives of methyl linoleate and methyl linolenate by negative chemical ionization mass spectroscopy. Lipids 28(2):125-133 (1993).
Gallon et al., The reaction of low levels of nitrogen dioxide with methyl linoleate in the presence and absence of oxygen. Lipids 29(3):171-176 (1994).
Garde, I., Complexa, Inc. Completes $13 Million Series B Financing to Further Advance Clinical Development of CXA-10. FierceBiotech, Jun. 4, 2014, pp. 1-2 (2014).
Gavin III et al., Reducing cardiovascular disease risk in patients with type 2 diabetes: a message from the National Diabetes Education Program. Am. Fam. Physician 68(8):1569-15674 (2003).
Geiger, S.S. et al., Chrono-immunology: progress and challenges in understanding links between the circadian and immune systems. Immunology 146(3):349-358 (2015).
Genders et al., cGMP phosphodiesterase inhibition improves the vascular and metabolic actions of insulin in skeletal muscle. Am J Physiol Endocrinol Metab. 301(2):E342-E350 (2011).
Gladwin et al., Role of circulating nitrite and S-nitrosohemoglobin in the regulation of regional blood flow in humans. Proc. Natl. Acad. Sci. 97(21):11482-11487 (2000).
Gladwin et al., S-nitrosohemoglobin is unstable in the reductive erythrocyte environment and lacks O2/NO-linked allosteric function. J Biol. Chem. 277(31):27818-27828 (2002).
Gladwin et al., The emerging biology of the nitrite anion. Nat. Chem. Biol. 1(6):308-314 (2005).
Glauser et al., The inflammatory response and tissue damage. The example of renal scars following acute renal infection. Pediatric Nephrology 1(4):615-622 (Abstract from PubMed website Jan. 22, 2016) (1987).
Goodman & Gilman's The Pharmacological Basis a/Therapeutics, Ninth Edition 1996, McGraw-Hill Book Company, New York, Appendix II, 1707-1711 (TOC) (1996).
Goodman & Gilman's The Pharmacological Basis a/Therapeutics, Sixth Edition 1980, MacMillan Publishing Co., New York (TOC) (1980).
Goodman & Gilman's The Pharmacological Basis a/Therapeutics, Tenth Edition 2001, McGraw-Hill Book Company, New York (TOC) (2001).
Gorczynski et al., Evaluation of nitroalkenes as nitric oxide donors. Bioorg. Med. Chem. Lett. 17:2013-2017 (2007).
Gorczynski et al., Regio—and stereospecific synthesis and nitric oxide donor properties of (E)-9- and (E)-10-nitrooctadec-9-enoic acids. Org. Lett. 8(11):2305-2308 (2006).
Gregory et al., 5-HT3 Receptor antagonists for the prevention of chemotherapy-induced nausea and vomiting: a comparison of their pharmacology and clinical efficacy. Drugs 55(2):173-189 (1998).
Grisham, Myoglobin-catalyzed hydrogen peroxide dependent arachidonic acid peroxidation. Free Radic. Biol. Med. 1:227-232 (1985).
Groeger et al., Cyclooxygenase-2 generates anti-inflammatory mediators from omega-3 fatty acids. Nat. Chem. Bio. 6:433-441 (2010).
Groeger et al., Discovery, structural characterization and quantification of novel inflammatory-induced electrophilic fatty acid derivatives. Free Radical Bio. & Med. 45(1):S134 (2008).
Groeger et al., Signaling actions of electrophiles: anti-inflammatory therapeutic candidates. Malec. Interven. 10(1):39-50 (2010).
Guindon et al., A simple, fast, and accurate algorithm to estimate large phylogenies by maximum likelihood. Systematic Bio. 52(5):696-704 (2003).

(56) References Cited

OTHER PUBLICATIONS

Guindon et al., Estimating maximum likelihood phylogenies with PhyML. Methods in Molecular Bio. 537:113-137 (2009).
Guo et al., Atypical PKCI transduces electrophilic fatty acid signaling in pulmonary epithelial cells. Nitric Oxide 25:366-372 (2011).
Gutierrez et al., Nitric oxide regulation of superoxide-dependent lung Injury: oxidant-protective actions of endogenously produced and exogenously administered nitric oxide. Free Radic. Biol. Med. 21(1):43-52 (1996).
Hackam, et al., Translation of Research Evidence From Animals to Humans;JAMA, 296(14), 2006, 1731-1732.
Hartmann et al., A randomized trial comparing the nephrotoxicity of cisplatin/ifosfamide-based combination chemotherapy with or without amifostine in patients with solid tumors. Investigational New Drugs 18:281-289 (2000).
Hogg et al., Inhibition of low-density lipoprotein oxidation by nitric oxide potential role in atherogenesis. FEBS Lett. 334(2):170-174 (1993).
Hogg et al., Reactions of nitric oxide with nitronyl nitroxides and oxygen: prediction of nitrate formation by kinetic simulation. Free Radic. Res. 22(1):47-56 (1995).
Hogg, The biochemistry and physiology of S-nitrosothiols. Annu. Rev. Pharmacol. Toxicol. 42:585-600 (2002).
Ichikawa et al., Nitroalkenes suppress lipopolysaccharide-induced signal transducer and activator of transcription signaling in macrophages: a critical role of mitogen-activated protein kinase phosphatase 1. Endocrinology 149(8):4086-4094 (2008).
Ignarro et al., Endothelium-derived relaxing factor from pulmonary artery and vein possesses pharmacologic and chemical properties identical to those of nitric oxide radical. Circ. Res. 61:866-879 (1987).
Ignarro et al., Pharmacological evidence that endothelium-derived relaxing factor is nitric oxide: use of pyrogallol and superoxide dismutase to study endothelium-dependent and nitric oxide-elicited vascular smooth muscle relaxation. J Pharmacol. Exp. Ther. 244(1):181-189 (1988).
Iles et al., Fatty acid transduction of nitric oxide signaling: nitrolinoleic acid mediates protective effects through regulation of the ERK pathway. Free Radic. Biol. Med. 46:866-875 (2009).
International Application No. PCT/US2017/040160 International Search Report and Written Opinion dated Oct. 9, 2017.
International Preliminary Report on Patentability for PCT/US2009/0047825 dated Jan. 6, 2011.
International Preliminary Report on Patentability issued in corresponding PCT/US2012/051304, 1-8 (Mar. 6, 2014).
International Preliminary Report on Patentability issued in corresponding PCT/US2012/059722, 1-9 (Apr. 24, 2014).
International Search Report and Written Opinion dated Dec. 4, 2009, in corresponding PCT/US2009/002628.
International Search Report and Written Opinion mailed Apr. 21, 2015 corresponding to PCT/US2014/065203.
International Search Report and Written Opinion mailed Aug. 19, 2013 corresponding to PCT/US2012/059722.
International Search Report and Written Opinion mailed Jul. 13, 2011 corresponding to PCT/US2010/051059.
International Search Report and Written Opinion mailed Jun. 2, 2013 corresponding to PCT/US2013/024476.
International Search Report and Written Opinion mailed Jun. 30, 2009 corresponding to PCT/US2009/041018.
International Search Report and Written Opinion mailed Mar. 23, 2012 corresponding to PCT/US2011/04201.
International Search Report and Written Opinion mailed Mar. 5, 2010 corresponding to PCT/US2009/047825.
International Search Report and Written Opinion mailed Nov. 1, 2012 corresponding to PCT/US2012/051304.
International Search Report and Written Opinion mailed Nov. 27, 2014 corresponding to PCT/US2014/047073.
International Search Report and Written Opinion mailed Oct. 12, 2006 corresponding to International Patent Application No. PCT/US2005/014305.
International Search Report and Written Opinion mailed Oct. 24, 2008 corresponding to International Patent Application No. PCT/US2008/009274.
International Search Report PCT/US2010/002141 dated Nov. 24, 2010.
Itoh et al., Synthesis of docosahexaenoic acid derivatives designed as novel PPARy agonists and antidiabetic agents. Bioorg.Med. Chem. 14:98-108 (2006).
Janero et al., Differential nitros(yl)ation of blood and tissue constituents during glycerol trinitrate biotransformation in vivo. PNAS 101(48):16958-16963 (2004).
Jasuja et al.: PDE-9 Inhibition Combined with Hydroxyurea Is Beneficial in Vaso-Occlusive Crisis in Mouse Model of Sickle Cell Disease. The American Society of Hematology; 124(21):2694 (2014).
Jeong et al., Fenofibrate prevents obesity and hypertriglyceridemia in low-density lipoprotein receptor-null mice. Metabolism 53(5):607-613 (2004).
Jimenez-Estrada et al., Allyic nitration of 3-sitosterol and cholesterol acetate: preparation of 7-nitro derivatives. Steroid 62:500-503 (1997).
Jordan, V. C., "Tamoxifen: a most unlikely pioneering medicine" Nature Reviews: Drug Discovery, 2, 2003, 205.
Jourd'Heuil et al., The oxidative and nitrosative chemistry of the nitric oxide/superoxide reaction in the presence of bicarbonate. Arch. Biochem. Biophys. 365(1):92-100 (1999).
Junping et al., Pharmacokinetics and antitumor effects of vincristine carried microemulsions composed of PEG-lipid, oleic acid, vitamin E and cholesterol. Int. J Pharm. 251(1-2):13-21, Abstract (2003).
Kalliokoski, A. et al., Impact of OATP transporters on pharmacokinetics. British Journal of Pharmacology 158(3):693-705 (2009).
Kansanen et al., Nrf2-dependent and -independent responses to nitro-fatty acids in human endothelial cells: identification of heat shock response as the major pathway activated by nitro-oleic acid. J Biol. Chem. 284(48):33233-33241 [1-34] (2009).
Karp et al., Clinical and biologic activity of the farnesyltransferase inhibitor RI 15777 in adults with refractory and relapsed acute leukemias: a phase 1 clinical-laboratory correlative trial. Blood 97(11):3361-3369 (2001).
Katoh et al., Recent developments in the MAFFT multiple sequence alignment program. Briefings in Bioinformatics 9(4):286-298 (2008).
Kelley et al.: Fatty acid nitroalkenes ameliorate glucose intolerance and pulmonary hypertension in high-fat diet-induced obesity. Cardiovascular Research. 101(3):352-363 (2014).
Kelley et al., Nitro-oleic acid, a novel and irreversible inhibitor of xanthine oxidoreductase. J Biol. Chem. 283(52):36176-36184 (2008).
Khoo et al., Activation of vascular endothelial nitric oxide synthase and heme oxygenase-1 expression by electrophilic nitro-fatty acids. Free Radic. Bio. Med. 48:230-239 (2010).
Khoo et al., Electrophilic nitro-fatty acids: anti-inflammatory mediators in the vascular compartment. Curr. Opn. Pharml. 10:179-184 (2010).
Kim et al., Bisubstrate ketone analogues as serotonin N-acetyltransferase inhibitors. J Med. Chem. 44(15):2479-2485 (2001).
Kim et al., The effect of PPAR-y agonist on glucose metabolism and insulin sensitivity in non-obese type 2 diabetic rat models. Diabetes Jun. 1, 2006, American Diabetes Association 55: Suppl. 1:A483 (2006).
Kissner et al., Formation and properties of peroxynitrite as studied by laser flash photolysis, high-pressure stopped-flow technique, and pulse radiolysis. Chem. Res. Toxicol. 10:1285-1292 (1997).
Kliewer et al. A prostaglandin J2 metabolite binds peroxisome proliferatory-activated receptor y and promotes adipocyte differentiation. Cell 83:813-819 (1995).
Kliewer et al., Fatty acids and eicosanoids regulate gene expression through direct interactions and peroxisome proliferator-activated receptors a and y Proc. Natl. Acad. Sci. 94:4318-4323 (1997).
Klinke et al.: Protective Effects of 10-nitro-oleic Acid in Hypoxia-Induced Murine Model of Pulmonary Hypertension. American Journal of Respiratory Dell and Molecular Biology. 51(1):155-162 (2014).
Kobayshi, The reaction of nitrogen dioxide with lung surface components: the reaction with cis-9octadecenoic acid. Chemosphere 12(9/10):1317-1325 (1983).

(56) References Cited

OTHER PUBLICATIONS

Koenitzer et al., Redox signaling in inflammation: interactions of endogenous electrophiles and mitochondria in cardiovascular disease. Ann. NY Acad. Sci. 1203:45-52 (2010).
Konig, J. et al., Transporters and drug-drug interactions: important determinants of drug disposition and effects. Pharmacological Review 65(3):944-66 (2013).
Kunin, Urinary tract infections in females. Clinical Infectious Diseases 18:1-10 (1994).
Lai et al., Reactions of dinitrogen pentoxide and nitrogen dioxide with 1-palmitoyl-2-oleoyl-sn-glycero-3-phosphocholine. Lipids 26(4):306-314. Abstract (1991).
Larfars et al., Activation of nitric oxide release and oxidative metabolism by leukotrienes B4, C4, and D4 in human polymorphonuclear leukocytes. Blood 93(4):1399-1405 (1999).
Lee et al., Peroxisome proliferators-activated receptor-yin macrophage lipid homeostasis. Trends Endocrinol. Metab. 13(8):331-335 (2002).
Lee et al., Rosiglitazone ameliorates cisplatin-induced renal injury in mice. Nephrol. Dial. Transplant. 21:2096-2105 (2006).
Levy et al., Lipid mediator class switching during acute inflammation: signals in resolution. Nat. Immunol. 2(7):612-619 (2001).
Li et al., Differential inhibition of macrophage foam-cell formation and atherosclerosis in mice by PPAR alpha, betta/delta, and gamma. J Clin. Invest. 114(11):1564-1576 (2004).
Li et al., Molecular recognition of nitrated fatty acids by PPAR gamma. Nat. Struct. Mol. Biol. 15(8):865-867 [1-3] (2008).
Li et al., PPARa ligand protects during cisplatin-induced acute renal failure by preventing inhibition of renal FAO and PDC activity. Am. J Physiol. Renal Physiol. 286:F572-F580 (2004).
Lim et al., Nitrolinoleate, a nitric oxide-derived mediator of cell function: synthesis, characterization, and vasomotor activity. Proc. Natl. Acad. Sci. 99(25):15941-15946 (2002).
Lima et al., Characterization of linoleic acid nitration in human blood plasma by mass spectrometry. Biochem. 41(34):10717-10722 (2002).
Lima et al., Cholesteryl nitrolinoleate, a nitrated lipid present in human blood plasma and lipoproteins. J Lipid Res. 44:1660-1666 (2003).
Lima et al., Nitrated lipids decompose to nitric oxide and lipid radicals and cause vasorelaxation. Free Radical Bio. Med., Elsevier Sciences 39(4):532-539 (2005).
Liu et al., Accelerated reaction of nitric oxide with O2 within the hydrophobic interior of biological membranes. Proc. Natl. Acad. Sci. 95:2175-2179 (1998).
Liu et al., Combined losartan and nitro-oleic acid remarkably improves diabetic nephrophaty in mice. Am. J Physiol. Renal Physiol. 305:FI555-F1562 (2013).
Liu et al., Nitrol-oleic acid protects the mouse kidney from ischemia and reperfusion injury. Am. J Physiol. Renal Physiol. 295(4):F942-F949 (2008).
Liu et al.: Nitro-oleic acid protects against adriamycin-induced nephropathy in mice. Am J Physiol Renal Physiol. 305(11):F1533-F1541 (2013).
Lopez et al., Second generation of a-tocopherol analogs-nitric oxide donors: synthesis, physiochemical, and biological characterization. Bioorg. Med. Chem. 15:6262-6272 (2007).
Loytynoja et al., An algorithm for progressive multiple alignment of sequences with insertions. PNAS 102(30):10557-10562 (2005).
Lundberg et al., Nitrate and nitrite in biology, nutrition and therapeutics. Nat. Chem. Bio. 5(12):865-869 (2009).
Luzzio, The Henry reaction: recent examples. Tetrahedron 57:915-945 (2001).
Ma et al., Hydrohalogenation reaction of substituted 1, 2-allenic carboxylic acids, esters, amides, nitriles, and diphenyl phosphine oxides. Synthesis (5):713-730 (2001).
Manini et al., Chemistry of nitrated lipids: remarkable instability of 9-nitrolinoleic acid in neutral aqueous medium and a novel nitronitrate ester product by concurrent autoxidation/nitric oxide-release pathways. J Org Chem. 73(19):7517-7525 (2008).
March, Effects of Structure on Reactivity. Advanced Organic Chemistry (1977 edition), McGraw-Hill Book Company, New York, 251-259 (1977).
Marnett et al., Regulation of prostaglandin biosynthesis by nitric oxide is revealed by targeted deletion of inducible nitric-oxide synthese. J Biol. Chem. 275(18):13427-13430 (2000).
Marshall et al., Nitrosation and oxidation in the regulation of gene expression. FASEB Journal 14:1889-1900 (2000).
Martini, S. et al., Integrative biology identifies shared transcriptional networks in CKD. Journal of the American Society of Nephrology 25:2559-2572 (2014).
Marx et al., Peroxisome proliferator-activated receptors and atherogenesis: regulators of gene expression in vascular cells. Circ. Res. 94(9):1168-1178 (2004).
Mcintyre et al., Identification of an intracellular receptor for lysophosphatidic acid (LPA): LPA is a transcellular PPARy agonist. Proc. Natl. Acad. Sci. 100(1):131-136 (2003).
Mclean, Iodostarin. Archives of Internal Medicine 10:509 (1912).
Mehats, C. et al., (2002) "Cyclic Nucleotide Phosphodiesterases and their Role in Endocrine Cell Signaling" Trends In Endocrinol. & Metab. 13:29-35.
Menendez et al., Effects of gama-linolenic acid and oleic acid on paclitaxel cytotoxicity in human breast cancer cells. European J of Cancer (Oxford, England: 1990) 37(3):402-213 (2001).
Messerschmidt et al., Handbook of Metalloproteins 2001, Hoboken, NJ, John Wiley & Sons, Inc. (abstract) (2001).
Metabolite definition at https:/www.nlm.nih.gov/medlineplus/ency/article/002258.htm (retrieved from the internet Jan. 21, 2016).
Meyer et al., Uremia. New Engl. J Med. 357:1316-1325 (2007).
Miguel et al., Inhibition of phosphodiesterase 9A reduces cytokine-stimulated in vitro adhesion of neutrophils from sickle cell anemia individuals. Inflammation Research 60(7):633-42 (2011).
Minghetti, Cyclooxygenase-2 (COX-2) in inflammatory and degenerative brain diseases. J Neuropathol. Exp. Neural. 63(9):901-910 (2004).
Miranda et al., The Chemical Biology of nitric oxide. nitric oxide: Biology and Pathobiology 2000, Academic Press, San Diego, 41-55 (2000).
Mitschke et al., 9- and 10-Nitro-oleic acid do not interfere with the GC-MS quantitative determination of nitrite and nitrate in biological fluids when measured as their pentalfluorobenzyl derivatives. J Chromatography B. 85(1):287-291 (2007).
Montuschi et al., Isoprostanes: markers and mediators of oxidative stress. FASEB J. 18:1791-1800 (2004).
Morgan et al., Use of animal models of human disease for nonclinical safety assessment of novel pharmaceuticals. Toxicol. Pathol. 41(3):508-518 (2013).
Mukherjee et al., A selective peroxisome proliferator-activated receptor-gamma (PPARgamma) modulator blocks adipocyte differentiation but stimulates glucose uptake in 3T3-L1 adipocytes. Mol. Endocrinol. 14:1425-1433. (2000).
Nadtochiy et al. Mitochondrial nitroalkene formation and mild uncoupling in ischaemic preconditioning: implications for cardioprotection. Card. Res. Adv. Access 2008, 1-8 (2008).
Nadtochiy et al., Nitroalkenes confer acute cardioprotection via adenine nucleotide transloase I. J Biol. Chem. 287(5):3573-3580 (2012).
Nagano et al., Use of tacrolimus, a potent antifibrotic agent, in bleomycin-induced lung fibrosis. Eur. Respir. J. 27:460-469 (2006).
Nagasaki et al., Phosphodiesterase type 9 (PDE9) in the human lower urinary tract: an immunohistochemical study. BJU International 109(6):934-940 (2012).
Nagy et al., Oxidized LDL regulates macrophage gene expression through ligand activation of PPARy. Cell 93:229-240 (1998).
Napolitano et al., Acid-induced structural modifications of unsaturated fatty acids and phenolic olive oil constituents by nitrite ions: a chemical assessment. Chem. Res. Toxicol.17:1329-1337 (2004).
Napolitano et al., Acid-promoted reactions of ethyl linoleate with nitrite ions: formation and structural characterization of isomeric nitroalkene, nitrohydroxy, and novel 3-nitro-1,5-hexadiene and 1,5-Dinitro-1,3-pentadiene products. J Org. Chem. 65(16):4853-4860 (2000).

(56) References Cited

OTHER PUBLICATIONS

Napolitano et al., The acid-promoted reaction of ethyl linoleate with nitrite. New insights from 15N-labelling and peculiar reactivity of a model skipped diene. Tetrahedron 58:5061-5067 (2002).
Narayan et al., Serine threonine protein kinases of mycobacterial genus: phylogeny to function. Physiological Genomics 29:66-75 (2007).
Nathan, Nitric oxide as a secretory product of mammalian cells. FASEB J. 6:3051-3064 (1992).
Newman et al., Optimized thiol derivatizing reagent for the mass spectral analysis of distributed epoxy fatty acids. J Chromato. 925:223-240 (2011).
Niebisch et al., Corynebacterial protein kinase G controls 2-oxoglutarate dehydrogenase activity via the phosphorylation status of the Odhl protein. J Biol. Chem. 281(18):12300-12307 (2006).
NIH US National Library of Medicine, FIRSTx—A Study of Oral CXA-10 in Primary Focal Segmental Glomerusclerosis (FSGS). NCT03422510, Feb. 5, 2018, pp. 1-10 (2018).
Notredame et al., T-Coffee: A novel method for fast and accurate multiple sequence alignment. J Malec. Bio. 302:205-217 (2000).
Nott et al., An intramolecular switch regulates phosphoindependent FHA domain interactions in *Mycobacterium tuberculosis*. Sci. Signaling 2(63):ra 12 (2009).
O'Donnell et al., 15-Lipoxygenase catalytically consumes nitric oxide and impairs activation of guanylae cyclase. J Biol. Chem. 274(29):20083-20091 (1999).
O'Donnell et al., Catalytic consumption of nitric oxide by prostagladin H synthase-I regulates platelet function. J Biol. Chem. 275(49):38239-38244 (2000).
O'Donnell et al., Interactions between nitric oxide and lipid oxidation pathways: implications for vascular disease. Circ. Res. 88:12-21 (2001).
O'Donnell et al., Nitration of unsaturated fatty acids by nitric oxide-derived reactive nitrogen species peroxynitrite, nitrous acid, nitrogen dioxide, and nitronium ion. Chem. Res. Toxicol. 12(1):83-92 (1999).
O'Donnell et al., Nitric oxide inhibition of lipid peroxidation: kinetics of reaction with lipid peroxyl radicals and comparison with a-tocopherol. Biochem. 36(49):15216-15223 (1997).
O'Hare et al., Regulation of glutamate metabolism by protein kinases in mycobacteria. Mol. Microbio. 70(6):1408-1423 (2008).
Ono et al., A convenient procedure for the conversion of E-nitroalkenes to (Z)-nitroalkenes via erythro—nitroselenides. J Chem. Soc., Chem Commun. 20:1550-1551 (1987).
Ortiz-Lombardia et al., Crystal structure of the catalytic domain of the PknB serine/threonine kinase from *Mycobacterium tuberculosis*. J Biol. Chem. 278(15):13094-13100 (2003).
Padmaja, The reaction of nitric oxide with organic peroxyl radicals. Biochem. Biophvs. Res. Commun. 195(2):539-544 (1993).
Park et al., Modulation of tumor necrosis factor-related apoptosis-inducing ligand-induced apoptosis by chemotherapy in thyroid cancer cell lines. Thyroid 13(12):1103-1110 (2003).
Pawliczak et al., 85-kDa cytosolic phospholipase A2 mediates peroxisome proliferator-activated receptor y activation in human lung epithelial cells. J Biol. Chem. 277:33153-33163 (2002).
PCT International Search Report and Written Opinion for PCT/US16/55206, Dec. 23, 2016.
PCT/CN2012/070718 International Search Report and Written Opinion dated Sep. 13, 2012.
PCT/EP2012/069936 International Search Report and Written Opinion dated Nov. 14, 2012.
PCT/EP2013/051451 International Search Report and Written Opinion dated Feb. 26, 2013.
PCT/EP2016/065964 International Search Report and Written Opinion dated Aug. 11, 2016.
PCT/US2018/034566 International Search Report and Written Opinion dated Aug. 21, 2018.
PCT/US2019/033835 International Preliminary Report on Patentability dated Dec. 1, 2020.
PCT/US2019/033835 International Search Report and Written Opinion dated Aug. 9, 2019.
PCT/US2019/048898 International Preliminary Report on Patentability dated Mar. 2, 2021.
PCT/US2019/048898 International Search Report and Written Opinion dated Nov. 25, 2019.
PCT/US2020/026696 International Preliminary Report on Patentability dated Oct. 14, 2021.
PCT/US2020/026696 International Search Report and Written Opinion dated Jun. 30, 2020.
PCT/US2020/031659 International Search Report and Written Opinion dated Jul. 31, 2020.
PCT/US2021/045765 Invitation to Pay Additional Fees dated Oct. 26, 2021.
Pharma Medica 20(5):199-210 (2002) (in Japanese with brief English relevance).
Pryor et al., Reaction of nitrogen dioxide with alkenes and polyunsaturated fatty acids: addition and hydrogen abstraction mechanisms. J Amer. Chem. Soc. 104:6685-6692 (1982).
PubChem CID 71550282 https://pubchem.ncbi.nlm.nih.gov/compound/71550282 (2013).
Punchard et al., The Journal of Inflammation Editorial; The Journal of Inflammation September, BioMed Central, 1(1):1-4 (2004).
Quijano et al., Reaction of peroxynitrite with Mn-superoxide dismutase: role of the metal center in decomposition kinetics and nitration. J of Biol. Chem. 276(15):11631-11638 (2001).
Radi et al., Peroxynitrite oxidation of sulfhydryls: the cytotoxic potential of superoxide and nitric oxide. J Biol. Chem. 266(7):4244-4250 (1991).
Radi et al., Peroxynitrite reactions with carbon dioxide-bicarbonate. Methods Enzymol. 301(37):353-367 (1999).
Ranu et al., Highly selective reduction of conjugated nitroalkenes with zinc borohydride in DME. Tetrahedron Letters 32(29):3579-3582 (1991).
Rassaf et al., Concomitant presence of n-nitroso and s-nitroso proteins in human plasma. Free Radic. Biol. Med. 33(11):1590-1596 (2002).
Rassaf et al., NO adducts in mammalian red blood cells: too much or too little? Nat. Med. 9(5):481-482 (2003).
Reema et al.: PDE-9 Inhibition combined with hydroxyurea is beneficial in vaso-occlusive crisis in mouse model of sickle cell disease. Blood. 124(21):1-2 (2014).
Remington's Pharmaceutical Sciences 1990, 18th Ed. (TOC).
Rosen et al., PPARy: a nuclear regulator of metabolism, differentiation, and cell growth. J Biol. Chem. 276(1):37731-37734 (2001).
Rowe et al., Handbook of Pharma. Excipients 2006, 5th Ed., Great Britain: Pharmaceutical Press, American Pharmacists Association (2006).
Rubbo et al., Forum on nitric oxide: chemical events in toxicity. Nitric oxide regulation of tissue free radical injury. Chem. Res. Toxicol. 9(5):809-820 (1996).
Rubbo et al., Nitric oxide inhibition of lipoxygenase-dependent liposome and low-density lipoprotein oxidation: termination of radical chain propagation reactions and formation of nitrogen-containing oxidized lipid derivatives. Arch. Biochem. Biophys. 324(1):15-25 (1995).
Rubbo et al., Nitric oxide reaction with lipid peroxyl radicals spares a-tocopherol during lipid peroxidation. J Biol. Chem. 275(25):10812-10818 (2000).
Rubbo et al., Nitric oxide regulation of superoxide and peroxynitrite-dependent lipid peroxidation. J Biol. Chem. 269(42):26066-26075 (1994).
Rudnick et al., Contrast-induced nephropathy: How it develops, how to prevent it. Cleveland Clinic J Med. 73(1):75-87 (2006).
Rudolph et al., Cardiovascular consequences when nitric oxide and lipid signaling converge. Circ. Res. 105:511-522 (2009).
Rudolph et al., Endogenous generation and protective effects of nitro-fatty acids in murine model of focal cardiac ischaemia and reperfusion. Cardiov. Res. Advance Access 1-12 (2009).
Rudolph et al., Nitro-fatty acid metabolome: saturation, desaturation,—oxidation, and protein adduction. J Biol. Chem. 284(3):1461-1473 (2009).

(56) References Cited

OTHER PUBLICATIONS

Rudolph et al., Nitro-fatty acids reduce atherosclerosis in apolipoprotein e-deficient mice. Ather. Thromb. Vasc. Bio. 30:938-945 (2010).
Rudolph et al., Transduction of redox signaling by electrophile-protein reactions. Science Signaling. 2(90):re7 [1-13] (2009).
Ryan et al., Diabetes and the Mediterranean diet: a beneficial effect of oleic acid on insulin sensitivity, adipocyte glucose transport and endothelium-dependent vasoreactivity. Q. J Med. 93:85-91 (2000).
Saffer et al., Choosing drug therapy for patients with hyperlipidemia. Am. Fam. Physic. 61(11):3371-3382 (2000).
Sarver et al., Analysis of peptides and proteins containing nitrotyrosine by matrix-assisted laser desorption/ionization mass spectrometry. J Am. Soc. Mass Spectrom. 12(4):439-448 (2001).
Satyanarayana et al., Steroselective synthesis of diacids by the nickel cyanide and phase-transfer-catalyzed carbonylation of alkynols. Novel dependency of product stereochemistry and optimum stirring speed on the nature of the phase-transfer agent. Organometallics 10:804-807 (1991).
Saulnier-Blache et al., A simple and highly sensitive radioenzymatic assay for lysophosphatidic acid quantification. J Lipid Res. 2000, vol. 41, 1947-1951 (2000).
Scarpini et al., Treatment of Alzheimer's disease: current status and new perspectives. Lancet Neural. 2:539-547 (2003).
Scherr et al., Structural basis for the specific inhibition of protein kinase G, a virulence factor of *Mycobacterium tuberculosis*. PNAS 104(29):12151-12156 (2007).
Schopfer et al., Covalent peroxisome proliferator-activated receptor gamma adduction by nitro-fatty acids: selective ligand activity and anti-diabetic signaling actions. J Biol. Chem. 285(16):12321-12333 (2010).
Schopfer et al., Detection and quantification of protein adduction by electrophilic fatty acids: mitochondrial generation of fatty acid nitroalkene derivatives. Free Radic. Biol. Med. 46:1250-1259 (2009).
Schopfer et al., Fatty acid transduction of nitric oxide signaling. Nitrolinoleic acid is a hydrophobically stabilized nitric oxide donor. J Biol. Chem. 280(19):19289-19297 (2005).
Schopfer et al., Nitrolinoleic acid: an endogenous peroxisome proliferator-activated receptor y ligand. Proc. Natl. Acad. Sci. 102(7):2340-2345 (2005).
Schopfer et al., NO-dependent protein nitration: a cell signaling event or an oxidative inflammatory response? Trends Biochem. Sci. 28:646-654 (2003).
Sculptoreanu et al., Nitro-oleic acid inhibits firing and activates TRPV-1 and TRPAI-mediated inward currents in dorsal root ganglion neurons from adult male rats. J Pharm. Expt. Thera. 333(3):883-895 (2010).
Serhan et al., Anti-inflammatory actions of neuroprotectin DI/protectin DI and its natural stereoisomers: assignments of dihydroxy-containing docosatrienes. J Immunology 176:1848-1859 (2006).
Setiadi et al., Vitamin E models. Conformational analysis and stereochemistry oftetralin, choman, thiochroman and selenochroman. J Molecular Structure (Theochem) 594:161-172 (2002).
Shaner et al., Designing herbicide tolerance based on metabolic alteration: the challenges and the future. In Pesticide Biotransformation in Plants and Microorganisms (Hall, J. et al.); ACS Symposium Series 2000, American Chemical Society; Washington DC, 353-374 (2000).
Sharpless et al., A mild procedure for the conversion of epoxides to allylic alcohols. The first organoselenium reagent. J Am. Chem. Soc. 95(8):2697-2699 (1973).
Sieker et al., Rubredoxin in crystalline state. Methods Enzymol. 243:203-216 (1994).
Simopoulos et al., Omega-3 fatty acids in inflammation and autoimmune diseases. J Amer. College of Nutrition 21(6):495-505 (2002).
Smith, Prostanoid biosynthesis and mechanisms of action. Am. Physiol. Soc. 263:F181-F191 (1992).
Snider et al., Oxidative and dehydrative cyclizations of nitroacetate esters with Mn (OAC). Tetrahedron 58(39):7821-7827 (2002).
Soding et al., HHsenser: exhaustive transitive profile search using HMM-HMM comparison. Nucleic Acids Res. 34:W374-378 (2006).
Strowig et al., Combination therapy using metformin or thiazolidinediones and insulin in the treatment of diabetes mellitus. Diabetes, Obesity, and Metabolism 7:633-641 (2005).
Subczynski et al., Permeability of nitric oxide through lipid bilayer membranes. Free Radic. Res. 24:343-349 (1996).
Szekely et al., A novel drug discovery concept for tuberculosis: inhibition of bacterial and host cell signaling. Immun. Letters 116(2):225-231 (2008).
Szoka et al., Comparative properties and methods of preparation of lipid vesicles (liposomes). Annual Review of Biophysics and Bioengineering 9:467-508 (1980).
Tang et al., Nitroalkenes induce rat aortic smooth muscle cell apoptosis via activation of caspase-dependent pathways. Biochem. Biophvs. Res. Commun. 397:239-244 (2010).
Thatcher et al., Nitrates and no release: contemporary aspects in biological and medicinal chemistry. Free Radic. Biol. Med. 37(8)1122-1143 (2004).
Thomas et al., The biological lifetime of nitric oxide: implications for the perivascular dynamics of NO and O2. Proc. Natl. Acad. Sci. 98(1):355-360 (2001).
Tiwari et al., Key residues in *Mycobacterium tuberculosis* protein kinase G play a role in regulating kinase activity and survival in the host. J Biol. Chem. 284(40):27467-27479 (2009).
Tontonoz et al., mPPARy2: tissue-specific regulator of an adipocyte enhancer. Genes Dev. 8(10):1224-1234 (1994).
Tontonoz et al., Stimulation of adipogenesis in fibroblasts by PPARy2, a lipid-activated transcription factor. Cell 79:1147-1156 (1994).
Toth, High-density lipoprotein and cardiovascular risk. Circulation 109:1809-1812 (2004).
Trostchansky et al., Nitrated fatty acids: mechanisms of formation, chemical characterization, and biological properties. Free Rad. Biol. Med. 44:1887-1896 (2008).
Tsikas et al., Nitro-fatty acids occur in human plasma in the picomolar range: a targeted nitro-lipidomics GC-MS/MS study. Lipids 44:855-865. (2009).
Tzameli et al., Regulated production of a peroxisome proliferatory-activated receptor-gamma ligand during an early phase of adipocyte differentiation in 3T3-LI adipocytes. J Biol. Chem. 279(34):36093-36102 (2004).
United States Office Action, U.S. Appl. No. 15/283,887, Feb. 8, 2019, 24 pages.
United States Office Action, U.S. Appl. No. 15/283,887, Jun. 14, 2018, 21 pages.
United States Office Action, U.S. Appl. No. 15/283,887, Nov. 16, 2017, 11 pages.
U.S. Appl. No. 16/315,365 Office Action dated Jul. 9, 2020.
U.S. Appl. No. 16/315,365 Restriction Requirement dated Oct. 7, 2019.
U.S. Appl. No. 16/615,347 Office Action dated Oct. 16, 2020.
U.S. Appl. No. 16/615,347 Office Action dated Sep. 2, 2021.
U.S. Appl. No. 16/673,709 Restriction Requirement dated Jun. 9, 2020.
Van Beilen et al., Rubredoxins involved in alkane oxidation. J Biol. Chem. 184(6):1722-1732 (2002).
Van der Staay, J.F. et al. (2008) "The Novel Selective PDE9 Inhibitor BAY 73-6691 Improved Learning and Memory in Rodents" Neuropharma 55(5):908-918.
Vasil'Ev et al., The action of nitrogen dioxide upon erucic acid. Lomonosova 5:50-58 (English abstract) (1995).
Verhoest et al., 2009, "Identification of a Brain Penetrant PDE9A Inhibitor Utilizing Prospective Design and chemical Enablement as a Rapic Lead Optimization Strategy", Journal of Medicinal Chemistry, vol. 52, No. 24, pp. 7946-7949.
Vickers et al., IGF-1 treatment reduces hyperphagia, obesity, and hypertension in metabolic disorders induced by fetal programming. Endocrinol. 142(9):3964-3973 (2001).
Vidwans et al., Differential modulation of prostaglandin H synthase-2 by nitric oxide-related species in intact cells. Biochem. 40:11533-11542 (2001).

(56) References Cited

OTHER PUBLICATIONS

Villacorta et al., Nitro-linoleic acid inhibits vascular smooth muscle cell proliferation via the Keap1/Nrf2 signaling pathway. Am. J Physiol. Heart Circ. Physiol. 293(1):H770-H776 [1-9] (2007).

Villacorta et al., PPARy and its ligands: therapeutic implications in cardiovascular disease. Clin. Sci. 116:205-218 (2009).

Villacorta, L. et al., Electrophilic nitro-fatty acids inhibit vascular inflammation by disrupting LPS-dependent TLR4 signaling in lipid rafts. Cardiovascular Research 98(1):116-124 (2013).

Villarino et al., Proteomic identification of *M. tuberculosis* protein kinase substrates: PknB recruits GarA, a FHA domain-containing protein, through activation loop-mediated Interactions. J Mol. Bio. 350(5):953-963 (2005).

'Virtual Chembook' in www.elmhurst.edu/-chm/vchembook/55 lfattyacids.html (retrieved Dec. 12, 2012).

Von Knethen et al., Activation of peroxisome proliferator-activated receptor y by nitric oxide in monocytes/macrophages down-regulates p47phox and attenuates the respiratory burst. J Immunol. 169:2619-2626 (2002).

Walburger et al., Protein kinase G from pathogenic *Mycobacteria* promotes survival within macrophages. Sci. 304:1800-1804 (2004).

Wang et al., Constitutive activation of peroxisome proliferator-activated receptor-y suppresses pro-inflammatory adhesion molecules in human vascular endothelial cells. J Biol. Chem. 277(37):34176-34181 (2002).

Wang et al., Effects of endogenous PPAR agonist nitro-oleic acid on metabolic syndrome in obese Zucker rats. PPAR Res. Art. ID 601562, 1-7 (2010).

Wang et al., Nitro-oleic acid protects against endotoxin-induced endotoxemia and multiorgan injury in mice. Am. J Physiol. Renal Physiol. 298:F754-F762 (2010).

Wang, H. et al., Nitrooleic acid attenuates lipid metabolic disorders and liver steatosis in DOCA-salt hypertensive mice. PPAR Research 2015:480348 [1-9] (2015).

Weber et al., Fragmentation of bovine serum albumin by pepsin. 1. The origin of the acid expansion of the albumin molecule. J Biol. Chem. 239(5):1415-1423 (1964).

Wehenkel et al., Mycobacterial Ser/Tur protein kinases and phosphatases: physiological roles and therapeutic potential. Biochemica et Biophysica Acta 1784(1):193-202 (2008).

Woodcock, Synthesis of nitrolipids. All four possible diastereomers of nitrooleic acids: (E)- and (Z)-, 9- and 10-nitro-octadec-9-enoic acids. Organic Letters 2006, 8(18):3931-3934 (2006).

Wright et al., Fatty acid transduction of nitric oxide signaling: Nitrolinoleic acid potently activates endothelial heme oxygenase 1 expression. PNAS 103(11)4299-4304 (2006).

Wright et al., Human heme oxygenase-1 induction by nitro-linoleic acid is mediated by cyclic AMP, AP-1, and e-box response element interactions. Biochem. J. 422(2):353-361 DOI:BJ20090339 [1-31] (2009).

Wunder, F. et al., (2005) "Charachertization of the First Potent and Selective PDE9 Inhibitor Using a cGMP Reporter sell Line" Mol. Pharmacol_ 68(6):1775-1781.

Xu et al., Lysophosphatidic acid as a potential biomaker for ovarian and other gynecologic cancers. JAMA 280:719-723 (1998).

Zhang et al., Lysophosphatidic acid induces neointima formation through PPARgamma activation. J Ex Med. 199(6):763-774 (2004).

Zhang et al., Nitro-oleic acid inhibits angiotensin II-induced hypertension. Circ. Res. 107:540-548 (2010).

Zhang et al., Selective disruption of PPARgamma2 impairs the development of adipose tissue and insulin sensitivity. Proc. Natl. Acad. Sci. 101(29):10703-10708 (2004).

Zhou, M. et al., (1994) "Role of Guanylyl Cyclase and cGMP-dependent Protein Kinase in Long-Term Potentiation" Nature 36(6472):635-639.

Gawarkar et al. "Roller compaction: an overview", Int. J. Universal Pharm. Bio Sciences 2015, 4(3):67-76.

Fig. 4

Compound 1: Beats HU (hydroxyurea), Robust Efficacy**

**p≤0.05

| Model System | Data with Compound 1 |
|---|---|
| Erythroid Cell Lines (K562, UT-7) | Increased cGMP levels vs. HU; induction of HbF (RNA, protein etc.,) |
| SCD Patient Derived Cell Lines | F-cells % increase, increases in HbF |
| In-vivo SCD: Townes (RBC/WBC) | Statistically better results than HU across most RBC/WBC parameters |
| In-vivo SCD : Vaso Occulsion (WBC) | Better results vs. HU; combo Compound 1+HU shows early signs of synergism |
| In-Vivo Cognition: C57Bl/6J | No CNS activity; no change in locomotor activity or fear conditioning (other PDE9i showed changes) |

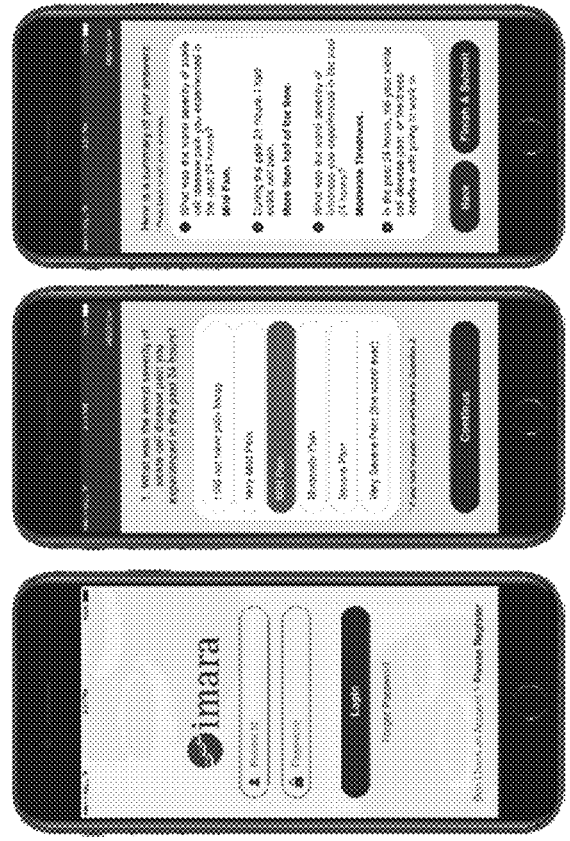

Fig. 8

Ph-2a: ePRO

Mobile device-based daily questionnaire

Assesses pain, fatigue, impact on daily living, medical care needs and pain medication usage Incorporates inputs from both UK and US KOLs Total of 9 questions

Not validated with repeat patient testing; will be used as exploratory endpoint in Compound 1 Phase 2a Automated reminders every evening

*No patient identifiers in app -- reconciliation occurs when all data is merged with the trial master file at end of study*

PDE9 INHIBITORS FOR TREATING SICKLE CELL DISEASE

CROSS-REFERENCE TO RELATED APPLICATIONS

This application is a continuation of International Application No. PCT/US2019/048898, filed Aug. 29, 2019, which claims the benefit of U.S. Provisional Application No. 62/725,725, filed Aug. 31, 2018, which is incorporated herein by reference in its entirety.

FIELD OF THE DISCLOSURE

The present disclosure relates to methods of making and using pharmaceutical compositions comprising cyclic guanylate monophosphate (cGMP)-specific phosphodiesterase type 9 inhibitors (hereinafter referred to as PDE9 inhibitors).

BACKGROUND

Sickle Cell Disease (SCD, also called sickle cell anemia (SCA)) is a genetic disorder leading to vaso-occlusive processes responsible for much of the mortality in SCD patients. SCD disease results from a point mutation in the hemoglobin (HBB) gene producing abnormal sickle hemoglobin (HbS or HbSS), which polymerizes and creates rigid and sticky sickled red blood cells. Sickled red blood cells result in chronic inflammation, elevated cell adhesion, oxidative stress, and endothelial dysfunction culminating in vaso-occlusive processes.

There is to date no cure for SCD. Treatment options include blood transfusion and treatment with the anti-cancer agent hydroxyurea. Blood transfusions correct anemia by increasing the number of normal, non-sickled red blood cells in circulation. Regular transfusion therapy can help prevent recurring strokes in children at high risk. Hydroxyurea (HU) has been approved for the treatment of SCD and shown to reduce the frequency of painful crisis and hospitalization. Unfortunately, HU is often poorly tolerated and its widespread use is limited by concerns about its potential impact on fertility and reproduction; challenges achieving and maintaining an efficacious dose due to its hematologic toxicities; and requirements for monthly monitoring (Heeney et al., *Pediatr Clin North Am.*, 2008, 55(2):483). In fact, it is estimated that only 1 out of 4 adult patients, and possibly even fewer, are treated with this drug (Stettler et al., *JAMA*, 2015, 313:1671). In addition, many patients are dosed with sub-efficacious doses of HU due to these challenges. Thus, novel, safe, and effective treatments that can be safely employed globally to prevent the morbid complications of SCD in patients of all ages are urgently needed.

There remains a need for treating SCD.

SUMMARY OF THE DISCLOSURE

The present disclosure provides methods of making and using Compound 1 and/or pharmaceutical compositions comprising Compound 1 or a pharmaceutically acceptable salt or polymorph thereof, to treat sickle cell disease.

In one aspect described herein, an oral pharmaceutical composition comprises: about 100 mg to about 300 mg of 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one (Compound 1), or a pharmaceutically acceptable salt, solvate, or polymorph thereof; a filler selected from about 4% to about 6% by weight of pre-gelatinized starch and/or from about 15% to about 50% microcrystalline cellulose; and a processing aid selected from about 1% to about 2.5% by weight of colloidal silicon dioxide and/or from about 0.5% to about 1.5% by weight of magnesium stearate, the pharmaceutical composition is in the form of a solid tablet suitable for administration to a patient. In some embodiments, the composition has a friability of no more than about 0.3% weight loss and a has a disintegration time of less than about 15 minutes, as determined by USP friability and USP disintegration tests. In some embodiments, the composition has at least one of a friability of no more than about 0.3% weight loss or a disintegration time of less than about 15 minutes, as determined by USP friability and USP disintegration tests. In some embodiments, the pharmaceutical composition above further comprises hydroxypropyl cellulose (HPC). In some embodiments, the hydroxypropyl cellulose (HPC) is present in an amount from about 0.4% to about 0.5% by weight. In some embodiments, the hydroxypropyl cellulose (HPC) is present in an amount of about 0.5% by weight. In some embodiments, the composition has a hardness of about 10 kPa and/or a thickness of about 4.50 to about 4.80 mm. In some embodiments, comprises about 100 mg, 200 mg, or about 300 mg of Compound 1, or a pharmaceutically acceptable salt, solvate, or polymorph thereof. In some embodiments, comprises about 300 mg of Compound 1, or a pharmaceutically acceptable salt, solvate, or polymorph thereof. In some embodiments, comprises about 5% by weight of pre-gelatinized starch. In some embodiments, comprises about 2% by weight of colloidal silicon dioxide. In some embodiments 1, comprises about 1% by weight of magnesium stearate. In some embodiments, the composition comprises pre-gelatinized starch, colloidal silicon dioxide, and magnesium stearate at a weight ratio of 5:2:1. In some embodiments, further comprises a coating selected from an enteric coating or Opadry® II white film coating. In some embodiments, the coating is about 2.5% by weight of the total tablet.

In another aspect described herein, an oral pharmaceutical composition comprises: from about 100 mg to about 300 mg of 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one (Compound 1), or a pharmaceutically acceptable salt, solvate, or polymorph thereof; about 5% by weight of pre-gelatinized starch; about 20% by weight of microcrystalline cellulose; about 2% by weight of colloidal silicon dioxide; and about 1% by weight of magnesium stearate, the pharmaceutical composition is in the form of a solid tablet. In some embodiments, the composition has a friability of no more than about 0.3% weight loss and/or a disintegration time of less than about 15 minutes, as determined by USP friability and USP disintegration tests. In some embodiments, further comprises about 0.5% by weight of hydroxypropyl cellulose (HPC). An oral pharmaceutical composition comprises 6-[(3S,4S)-4-methyl-1-(pyrimidin-2-ylmethyl) pyrrolidin-3-yl]-3-tetrahydropyran-4-yl-7H-imidazo[1,5-a] pyrazin-8-one (Compound 1), or a pharmaceutically acceptable salt, solvate, or polymorph thereof; the pharmaceutical composition is in the form of a solid tablet. In some embodiments, further comprises at least a filler. In some embodiments, the filler is microcrystalline cellulose or pre-gelatinized starch. In some embodiments, the composition comprises about 4% to about 6% by weight of pre-gelatinized starch. In some embodiments, the composition comprises about 15 mg to about 25 mg of pre-gelatinized starch per tablet. In some embodiments, the composition further comprises at least a processing aid. In some embodiments, the processing aid is colloidal silicon dioxide and/or magnesium stearate. In some embodiments, the composition comprises about 1% to about 2.5% by weight of colloidal silicon dioxide and/or about 0.5% to about 1.5% by weight of magnesium stearate. In some embodiments, the composition comprises about 6 mg to about 8 mg colloidal silicon dioxide and/or about 2 mg to about 4 mg of magnesium stearate per tablet. In some embodiments, comprises microcrystalline cellulose, pre-gelatinized starch, colloidal silicon dioxide, and magnesium stearate. In some embodiments, further comprises a coating selected from an enteric coating or Opadry® II white film coating. In some embodiments, the coating is about 2.5% by weight of the tablet. In some embodiments, the composition comprises about 20 mg to about 40 mg of the coating per tablet. In some embodiments, the composition comprises pre-gelatinized starch, colloidal silicon dioxide, and magnesium stearate at a weight ratio of 5:2:1. In some embodiments, Compound 1, or a pharmaceutically acceptable salt or polymorph thereof, is present in an amount of about 30 mg, 50 mg, 100 mg, 150 mg, 200 mg, 250 mg, 300 mg, or 350 mg. In some embodiments, Compound 1, or a pharmaceutically acceptable salt or polymorph thereof, is present in the composition in an amount from about 50% to about 80% or from about 60% to about 75% by weight of the solid tablet. In some embodiments, Compound 1, or a pharmaceutically acceptable salt or polymorph thereof, is present in the composition in an amount 65%, about 68%, about 70%, about 72%, or about 75% by weight of the solid tablet. In some embodiments, the composition has a friability and/or a disintegration time. In some embodiments, the composition has a friability of no more than 0.3% weight loss and/or a disintegration time of less than about 15 minutes, friability and disintegration time are determined by USP testing. In some embodiments, the composing further comprises 0.4% to about 0.5% by weight of hydroxypropyl cellulose.

In another aspect described herein, a method for treating sickle cell disease in a subject in need, comprises administering any of the pharmaceutical compositions above. In some embodiments, the pharmaceutical composition is taken with food. In some embodiments, the pharmaceutical composition is administered once per day, twice per day, or three times per day. In some embodiments, the pharmaceutical composition is administered once per day. In some embodiments, the pharmaceutical composition is administered for at least 4 weeks, 12 weeks, 16 weeks, or 24 weeks. In some embodiments, the method further comprises administering hydroxyurea (HU). In some embodiments, the method comprises administering to the subject about 0.3 mg/kg to about 6.0 mg/kg or from about 0.3 mg/kg to about 1.0 mg/kg of subjects body mass per day or per dose of Compound 1, or a pharmaceutically acceptable salt or polymorph thereof.

BRIEF DESCRIPTION OF THE DRAWINGS

FIG. 4 shows a chart of comparison between Compound 1 and hydroxyurea showing the superior efficacy of Compound 1.

FIG. 8 depicts, without limitation, a representative sampling of screenshots for use in a mobile device running software designed to track human impact of a pharmaceutical.

DETAILED DESCRIPTION

Figure 1:
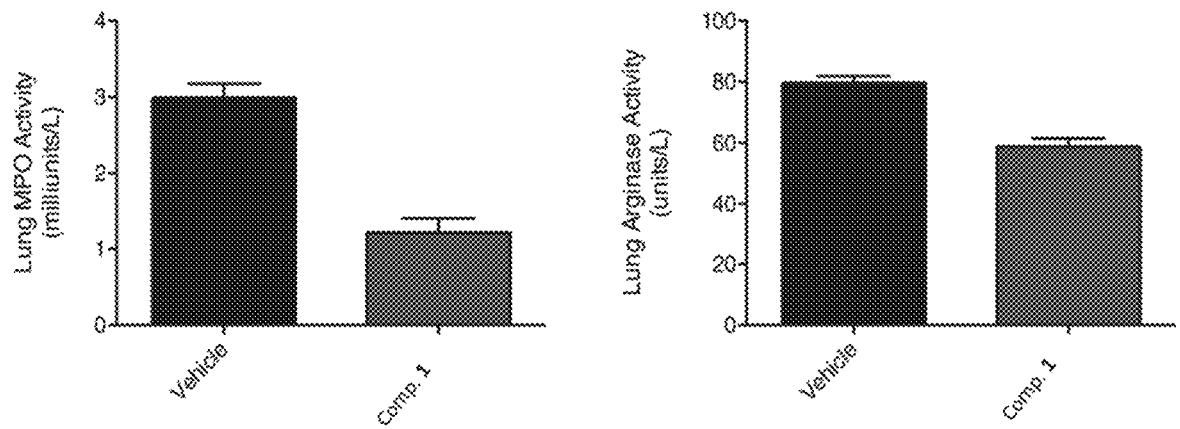
FIG. 1 shows Compound 1 reduces myeloid and neutrophil inflammatory markers in the lungs of Townes mice.

Phosphodiesterases (PDEs) are a family of enzymes degrading cyclic nucleotides and thereby regulating the cellular levels of second messengers throughout the entire body. PDEs represent attractive drug targets, as proven by a number of compounds that have been introduced to clinical testing and the market, respectively. PDEs are encoded by 21 genes that are functionally separated into 11 families differing with respect to kinetic properties, substrate selectivity, expression, localization pattern, activation, regulation factors and inhibitor sensitivity. The function of PDEs is the degradation of the cyclic nucleotide monophosphates cyclic Adenosine Monophosphate (cAMP) and/or Guanosine Monophosphate (cGMP), which are important intracellular mediators involved in numerous vital processes including the control of neurotransmission and smooth muscle contraction and relaxation.

PDE9 is cGMP specific ($K_m$ cAMP is >1000× for cGMP) and is hypothesized to be a key player in regulating cGMP levels as it has the lowest $K_m$ among the PDEs for this nucleotide. PDE9 is expressed throughout the brain at low levels with the potential for regulating basal cGMP.

In the periphery, PDE9 expression is highest in prostate, intestine, kidney and haematopoietic cells, enabling therapeutic potential in various non-CNS indications.

In the present disclosure, pharmaceutical compositions comprising PDE9 inhibitors are designed for treatment for Sickle Cell Disease (SCD).

Compounds of the Disclosure

In the context of the present disclosure, a compound is considered to be a PDE9 inhibitor if the amount required to reach the 50% inhibition level PDE9 is 10 micromolar or less, preferably less than 9 micromolar, such as 8 micromolar or less, such as 7 micromolar or less, such as 6 micromolar or less, such as 5 micromolar or less, such as 4 micromolar or less, such as 3 micromolar or less, more preferably 2 micromolar or less, such as 1 micromolar or less, in particular 500 nM or less. In preferred embodiments the required amount of PDE9 inhibitor required to reach the $IC_{50}$ level of PDE9 is 400 nM or less, such as 300 nM or less, 200 nM or less, 100 nM or less, or even 80 nM or less, such as 50 nM or less, for example 25 nM or less.

Throughout this application the notations $IC_{50}$ and IC50 are used interchangeably.

In some embodiments, the PDE9 inhibitor of the present disclosure has low or no blood brain barrier penetration. For example, the ratio of the concentration of a PDE9 inhibitor of the present disclosure in the brain to the concentration of it in the plasma (brain/plasma ratio) may be less than about 0.50, about 0.40, about 0.30, about 0.20, about 0.10, about 0.05, about 0.04, about 0.03, about 0.02, or about 0.01. In some embodiments, the brain/plasma ration is measured 30 min or 120 min after administration of the PDE9 inhibitor.

In some embodiments, the PDE9 inhibitor may be any imidazo pyrazinone PDE9 inhibitor disclosed in WO 2013/053690 and/or any imidazo triazinone PDE9 inhibitor disclosed in WO 2013/110768, the contents of each of which are incorporated herein by reference in their entirety.

In some embodiments, the PDE9 inhibitor is Compound 1 or a pharmaceutically acceptable salt, cocrystal, solvate, or polymorph thereof. A racemate form of Compound 1 and an anhydrous form of Compound 1 have been described in WO 2013/053690 and WO 2017/005786. In some embodiments, the PDE9 inhibitor is 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one (Compound 1), or a pharmaceutically acceptable salt or polymorph thereof. In some Compound 1 has the following structure:

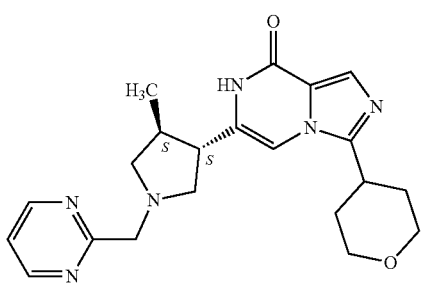

6-[(3S,4S)-4-methyl-1-(pyrimidin-2-ylmethyl)pyrrolidin-3-yl]-3-tetrahydropyran-4-yl-7H-imidazo[1,5-a]pyrazin-8-one; Formula $C_{21}H_{26}N_6O_2$; calculated molecular weight about 394 g/mol. In some embodiments, Compound 1 is enantiopure or substantially enantiopure.

Pharmaceutical Compositions

The present disclosure further provides a pharmaceutical composition comprising a therapeutically effective amount of any of the PDE9 inhibitors and a pharmaceutically acceptable carrier or diluent. In some embodiments, the present disclosure provides a pharmaceutical composition comprising a therapeutically effective amount of Compound 1, or a pharmaceutically acceptable salt or polymorph thereof, and a pharmaceutically acceptable carrier or diluent or excipient.

Pharmaceutically Acceptable Salts

The present disclosure also comprises salts of the PDE9 inhibitors, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this disclosure may exist in unsolvated as well as in solvated forms with pharmaceutically acceptable solvents such as water, ethanol, and the like. In general, the solvated forms are considered equivalent to the unsolvated forms for the purposes of this disclosure.

In some embodiments, the pharmaceutical composition comprises Compound 1 as the solvated, unsolvated, or crystalline form. In some embodiments, Compound 1 is present as the unsolvated form. In some embodiments, Compound 1 is present as the present as the crystalline form. In some embodiments, Compound 1 is present as a monohydrate crystalline form.

Formulations

The compounds of the disclosure may be administered alone or in combination with pharmaceutically acceptable carriers, diluents or excipients, in either single or multiple doses. The pharmaceutical compositions according to the disclosure may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, PA, 2013.

The pharmaceutical compositions may be specifically formulated for administration by any suitable route, such as oral, rectal, nasal, pulmonary, topical (including buccal and sublingual), transdermal, intracisternal, intraperitoneal, vaginal, and parenteral (including subcutaneous, intramuscular, intrathecal, intravenous, and intradermal) routes. It will be appreciated that the route will depend on the general health and age of the subject to be treated, the nature of the condition to be treated, and the active ingredient. In some embodiments, the pharmaceutical composition is formulated for oral administration to a subject. In some embodiments, the pharmaceutical composition is formulated as a tablet or pill. In some embodiments, the pharmaceutical composition is formulated as a solid tablet suitable for oral administration to a subject.

Pharmaceutical compositions for oral administration include solid dosage forms such as capsules, tablets, dragees, pills, lozenges, powders, and granules. Where appropriate, the compositions may be prepared with coatings, such as enteric coatings or they may be formulated so as to provide controlled release of the active ingredient such as sustained or prolonged release according to methods well known in the art. Liquid dosage forms for oral administration include solutions, emulsions, suspensions, syrups, and elixirs, either manufactured as such, or as a solid form for reconstitution prior to use.

Pharmaceutical compositions for parenteral administration include sterile aqueous and non-aqueous injectable solutions, dispersions, suspensions, or emulsions as well as sterile powders to be reconstituted in sterile injectable solutions or dispersions prior to use. Other suitable administration forms include, but are not limited to, suppositories, sprays, ointments, creams, gels, inhalants, dermal patches, and implants.

The present disclosure also provides a process for making a pharmaceutical composition comprising admixing a therapeutically effective amount of a compound of the present disclosure and at least one pharmaceutically acceptable carrier or diluent.

The compounds of this disclosure are generally utilized as the free substance or as a pharmaceutically acceptable salt thereof. Such salts are prepared in a conventional manner by treating a solution or suspension of a compound of the present disclosure with a pharmaceutically acceptable acid. Representative examples of suitable organic and inorganic acids are described above.

For parenteral administration, solutions of the compounds of the present disclosure in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of the present disclosure may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of the present disclosure and a pharmaceutically acceptable carrier are then readily administered in a variety of dosage forms suitable for the disclosed routes of administration. The formulations may conveniently be presented in unit dosage form by methods known in the art of pharmacy.

Pharmaceutical compositions of the present disclosure suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatine capsule in powder or pellet form or it may be in the form of a troche or lozenge. The amount of solid carrier will vary widely but will range from about 25 mg to about 1 g per dosage unit. In some embodiments, the solid carrier will be about 10 mg to about 150 mg per dosage unit. In some embodiments, the solid carrier will be about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 125 mg, about 10 mg to about 150 mg, about 20 mg to about 30 mg, about 20 mg to about 40 mg, about 20 mg to about 50 mg, about 20 mg to about 60 mg, about 20 mg to about 70 mg, about 20 mg to about 80 mg, about 20 mg to about 90 mg, about 20 mg to about 100 mg, about 20 mg to about 125 mg, about 20 mg to about 150 mg, about 30 mg to about 40 mg, about 30 mg to about 50 mg, about 30 mg to about 60 mg, about 30 mg to about 70 mg, about 30 mg to about 80 mg, about 30 mg to about 90 mg, about 30 mg to about 100 mg, about 30 mg to about 125 mg, about 30 mg to about 150 mg, about 40 mg to about 50 mg, about 40 mg to about 60 mg, about 40 mg to about 70 mg, about 40 mg to about 80 mg, about 40 mg to about 90 mg, about 40 mg to about 100 mg, about 40 mg to about 125 mg, about 40 mg to about 150 mg, about 50 mg to about 60 mg, about 50 mg to about 70 mg, about 50 mg to about 80 mg, about 50 mg to about 90 mg, about 50 mg to about 100 mg, about 50 mg to about 125 mg, about 50 mg to about 150 mg, about 60 mg to about 70 mg, about 60 mg to about 80 mg, about 60 mg to about 90 mg, about 60 mg to about 100 mg, about 60 mg to about 125 mg, about 60 mg to about 150 mg, about 70 mg to about 80 mg, about 70 mg to about 90 mg, about 70 mg to about 100 mg, about 70 mg to about 125 mg, about 70 mg to about 150 mg, about 80 mg to about 90 mg, about 80 mg to about 100 mg, about 80 mg to about 125 mg, about 80 mg to about 150 mg, about 90 mg to about 100 mg, about 90 mg to about 125 mg, about 90 mg to about 150 mg, about 100 mg to about 125 mg, about 100 mg to about 150 mg, or about 125 mg to about 150 mg. In some embodiments, the solid carrier will be about 10 mg, about 20 mg, about 30 mg, about 40 mg, about 50 mg, about 60 mg, about 70 mg, about 80 mg, about 90 mg, about 100 mg, about 125 mg, or about 150 mg. In some embodiments, the solid carrier will be at least about 10 mg, about 20 mg, about 30 mg, about 40 mg, about 50 mg, about 60 mg, about 70 mg, about 80 mg, about 90 mg, about 100 mg, or about 125 mg. In some embodiments, the solid carrier will be at most about 20 mg, about 30 mg, about 40 mg, about 50 mg, about 60 mg, about 70 mg, about 80 mg, about 90 mg, about 100 mg, about 125 mg, or about 150 mg per dosage unit. In some embodiments, the solid carrier will be about 150 mg to about 1,000 mg per dosage unit. In some embodiments, the solid carrier will be about 150 mg to about 175 mg, about 150 mg to about 200 mg, about 150 mg to about 300 mg, about 150 mg to about 400 mg, about 150 mg to about 500 mg, about 150 mg to about 600 mg, about 150 mg to about 700 mg, about 150 mg to about 800 mg, about 150 mg to about 900 mg, about 150 mg to about 1,000 mg, about 175 mg to about 200 mg, about 175 mg to about 300 mg, about 175 mg to about 400 mg, about 175 mg to about 500 mg, about 175 mg to about 600 mg, about 175 mg to about 700 mg, about 175 mg to about 800 mg, about 175 mg to about 900 mg, about 175 mg to about 1,000 mg, about 200 mg to about 300 mg, about 200 mg to about 400 mg, about 200 mg to about 500 mg, about 200 mg to about 600 mg, about 200 mg to about 700 mg, about 200 mg to about 800 mg, about 200 mg to about 900 mg, about 200 mg to about 1,000 mg, about 300 mg to about 400 mg, about 300 mg to about 500 mg, about 300 mg to about 600 mg, about 300 mg to about 700 mg, about 300 mg to about 800 mg, about 300 mg to about 900 mg, about 300 mg to about 1,000 mg, about 400 mg to about 500 mg, about 400 mg to about 600 mg, about 400 mg to about 700 mg, about 400 mg to about 800 mg, about 400 mg to about 900 mg, about 400 mg to about 1,000 mg, about 500 mg to about 600 mg, about 500 mg to about 700 mg, about 500 mg to about 800 mg, about 500 mg to about 900 mg, about 500 mg to about 1,000 mg, about 600 mg to about 700 mg, about 600 mg to about 800 mg, about 600 mg to about 900 mg, about 600 mg to about 1,000 mg, about 700 mg to about 800 mg, about 700 mg to about 900 mg, about 700 mg to about 1,000 mg, about 800 mg to about 900 mg, about 800 mg to about 1,000 mg, or about 900 mg to about 1,000 mg. In some embodiments, the solid carrier will be about 150 mg, about 175 mg, about 200 mg, about 300 mg, about 400 mg, about 500 mg, about 600 mg, about 700 mg, about 800 mg, about 900 mg, or about 1,000 mg. In some embodiments, the solid carrier will be at least about 150 mg, about 175 mg, about 200 mg, about 300 mg, about 400 mg, about 500 mg, about 600 mg, about 700 mg, about 800 mg, or about 900 mg. In some embodiments, the solid carrier will be at most about 175 mg, about 200 mg, about 300 mg, about 400 mg, about 500 mg, about 600 mg, about 700 mg, about 800 mg, about 900 mg, or about 1,000 mg per dosage unit.

In some embodiments, the solid carrier will be about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or about 1 g per dosage unit. If a liquid carrier is used, the preparation may be in the form of a syrup, emulsion, soft gelatine capsule or sterile injectable liquid such as an aqueous or non-aqueous liquid suspension or solution In some embodiments, the solid carrier will be about 1 g to about 2 g per dosage unit. In some embodiments, the solid carrier will be about 1 g to about 1.1 g, about 1 g to about 1.2 g, about 1 g to about 1.3 g, about 1 g to about 1.4 g, about 1 g to about 1.5 g, about 1 g to about 1.6 g, about 1 g to about 1.7 g, about 1 g to about 1.8 g, about 1 g to about 1.9 g, about 1 g to about 2 g, about 1.1 g to about 1.2 g, about 1.1 g to about 1.3 g, about 1.1 g to about 1.4 g, about 1.1 g to about 1.5 g, about 1.1 g to about 1.6 g, about 1.1 g to about 1.7 g, about 1.1 g to about 1.8 g, about 1.1 g to about 1.9 g, about 1.1 g to about 2 g, about 1.2 g to about 1.3 g, about 1.2 g to about 1.4 g, about 1.2 g to about 1.5 g, about 1.2 g to about 1.6 g, about 1.2 g to about 1.7 g, about 1.2 g to about 1.8 g, about 1.2 g to about 1.9 g, about 1.2 g to about 2 g, about 1.3 g to about 1.4 g, about 1.3 g to about 1.5 g, about 1.3 g to about 1.6 g, about 1.3 g to about 1.7 g, about 1.3 g to about 1.8 g, about 1.3 g to about 1.9 g, about 1.3 g to about 2 g, about 1.4 g to about 1.5 g, about 1.4 g to about 1.6 g, about 1.4 g to about 1.7 g, about 1.4 g to about 1.8 g, about 1.4 g to about 1.9 g, about 1.4 g to about 2 g, about 1.5 g to about 1.6 g, about 1.5 g to about 1.7 g, about 1.5 g to about 1.8 g, about 1.5 g to about 1.9 g, about 1.5 g to about 2 g, about 1.6 g to about 1.7 g, about 1.6 g to about 1.8 g, about 1.6 g to about 1.9 g, about 1.6 g to about 2 g, about 1.7 g to about 1.8 g, about 1.7 g to about 1.9 g, about 1.7 g to about 2 g, about 1.8 g to about 1.9 g, about 1.8 g to about 2 g, or about 1.9 g to about 2 g. In some embodiments, the solid carrier will be about 1 g, about 1.1 g, about 1.2 g, about 1.3 g, about 1.4 g, about 1.5 g, about 1.6 g, about 1.7 g, about 1.8 g, about 1.9 g, or about 2 g. In some embodiments, the solid carrier will be at least about 1 g, about 1.1 g, about 1.2 g, about 1.3 g, about 1.4 g, about 1.5 g, about 1.6 g, about 1.7 g, about 1.8 g, or about 1.9 g. In some embodiments, the solid carrier will be at most about 1.1 g, about 1.2 g, about 1.3 g, about 1.4 g, about 1.5 g, about 1.6 g, about 1.7 g, about 1.8 g, about 1.9 g, or about 2 g per dosage unit.

The pharmaceutical compositions of the disclosure may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

The pharmaceutical composition comprises PDE9 inhibitor Compound 1. The pharmaceutical composition comprises at least 10%, 20%, 30%, 40%, 50%, 60%, 70%, 80%, or 90% by weight of PDE9 inhibitors of the present disclosure. The pharmaceutical composition comprises at least about 1% to about 90% by weight of PDE9 inhibitors of the present disclosure. The pharmaceutical compositions comprises at least about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%. The pharmaceutical compositions comprise at least about 1%, about 10%, about 20%, about 30%, about 40%, about 50%, about 60%, about 70%, about 80%, or about 90%. The pharmaceutical compositions comprises at least at least about 1%, about 10%, about 20%, about 30%, about 40%, about 50%, about 60%, about 70%, or about 80%. The pharmaceutical compositions comprises at least at most about 10%, about 20%, about 30%, about 40%, about 50%, about 60%, about 70%, about 80%, or about 90% by weight of PDE9 inhibitors of the present disclosure. The pharmaceutical composition comprises at least about 90% to about 99.9% by weight of PDE9 inhibitors of the present disclosure. The pharmaceutical composition comprises at least about 90% to about 91%, about 90% to about 92%, about 90% to about 93%, about 90% to about 94%, about 90% to about 95%, about 90% to about 96%, about 90% to about 97%, about 90% to about 98, about 90% to about 99%, about 90% to about 99.9%, about 91% to about 92%, about 91% to about 93%, about 91% to about 94%, about 91% to about 95%, about 91% to about 96%, about 91% to about 97%, about 91% to about 98%, about 91% to about 99%, about 91% to about 99.9%, about 92% to about 93%, about 92% to about 94%, about 92% to about 95%, about 92% to about 96%, about 92% to about 97%, about 92% to about 98%, about 92% to about 99%, about 92% to about 99.9%, about 93% to about 94%, about 93% to about 95%, about 93% to about 96%, about 93% to about 97%, about 93% to about 98%, about 93% to about 99%, about 93% to about 99.9%, about 94% to about 95%, about 94% to about 96%, about 94% to about 97%, about 94% to about 98%, about 94% to about 99%, about 94% to about 99.9%, about 95% to about 96%, about 95% to about 97%, about 95% to about 98%, about 95% to about 99%, about 95% to about 99.9%, about 96% to about 97%, about 96% to about 98%, about 96% to about 99%, about 96% to about 99.9%, about 97% to about 98%, about 97% to about 99%, about 97% to about 99.9%, about 98% to about 99%, about 98% to about 99.9%, or about 99% to about 99.9%. The pharmaceutical composition comprises at least about 90%, about 91%, about 92%, about 93%, about 94%, about 95%, about 96%, about 97%, about 98%, about 99%, or about 99.9%. The pharmaceutical compositions comprises at least at least about 90%, about 91%, about 92%, about 93%, about 94%, about 95%, about 96%, about 97%, about 98%, or about 99%. The pharmaceutical composition comprises at least at most about 91%, about 92%, about 93%, about 94%, about 95%, about 96%, about 97%, about 98%, about 99%, or about 99.9% by weight of PDE9 inhibitors of the present disclosure. The pharmaceutical composition comprise at least 90%, 91%, 92%, 93%, 94%, 95%, 96%, 97%, 98%, or 99% by weight of PDE9 inhibitors of the present disclosure.

In some embodiments, Compound 1 or a pharmaceutically acceptable salt or polymorph thereof is formulated as a pharmaceutical composition for oral administration. For example, it may be in a solid tablet form. The composition for oral administration comprises at least a filler and/or a processing aid. The processing aid may be a glidant or a lubricant. The composition for oral administration may also comprise a coating. In some embodiments, the composition for oral administration comprises microcrystalline cellulose and/or pre-gelatinized starch as fillers. In some embodiments, the composition for oral administration comprises colloidal silicon dioxide and/or magnesium stearate as processing aids. In some embodiments, the composition for oral administration comprises Opadry® II white film coating. Opadry® II is a high productivity, water soluble, pH independent complete dry powder film coating system containing polymer, plasticizer and pigment which allows for immediate disintegration for fast, active release. In some embodiments, the composition for oral administration comprises purified water, which is removed during processing.

In some embodiments, the tablet comprises a coating between about 5% to about 20% by weight of the total weight of the tablet. In some embodiments, the tablet comprises a coating between about 0.5% to about 10%. In some embodiments, the tablet comprises a coating between about 0.5% to about 1%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 0.5% to about 10%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 9% to about 10%. In some embodiments, the tablet comprises a coating between about 0.5%, about 1%, about 2%, about 3%, about 4%, about 5%, about 6%, about 7%, about 8%, about 9%, or about 10%. In some embodiments, the tablet comprises a coating between at least about 0.5%, about 1%, about 2%, about 3%, about 4%, about 5%, about 6%, about 7%, about 8%, or about 9%. In some embodiments, the tablet comprises a coating between at most about 1%, about 2%, about 3%, about 4%, about 5%, about 6%, about 7%, about 8%, about 9%, or about 10%. In some embodiments, the tablet comprises a coating between about 0.5% about 5%, about 10%, about 15%, or about 20% by weight of the total weight of the tablet.

In some embodiments, the composition further comprises an enteric coating. An enteric coating is a polymer barrier applied on oral medication that prevents its dissolution or disintegration in the gastric environment. Tablets, mini-tablets, pellets and granules (usually filled into capsule shells) are the most common enteric-coated dosage forms. Most enteric coatings work by presenting a surface that is stable at the intensely acidic pH found in the stomach, but breaks down rapidly at a higher pH (alkaline pH). For example, they will not dissolve in the gastric acids of the stomach (pH ~3), but they will in the alkaline (pH 7-9) environment present in the small intestine. By preventing the drug from dissolving into the stomach, enteric coating may protect gastric mucosa from the irritating effects of the medication itself. When the drug reaches the neutral or alkaline environment of the intestine, its active ingredients can then dissolve and become available for absorption into the bloodstream. Materials used for enteric coatings include but are not limited to fatty acids, waxes, shellac, plastics, and plant fibers. Conventional materials used are solutions of film resins.

In some embodiments, the pharmaceutical composition comprises a filler. In some embodiments, the filler is pre-gelatinized starch. In the embodiment, the pharmaceutical composition comprises pre-gelatinized starch between about 4% to about 6% by weight of the total weight of the pharmaceutical composition. In some embodiments, the pharmaceutical composition comprises pre-gelatinized starch at about 4%, about 5%, or about 6% by weight of the total weight of the pharmaceutical composition.

In some embodiments, the filler is microcrystalline cellulose. In some embodiments, the pharmaceutical composition comprises microcrystalline cellulose at between about 15% to about 50% by weight of the total weight of the pharmaceutical composition. In some embodiments, the pharmaceutical composition comprises microcrystalline cellulose at about 50%, about 40%, about 30%, about 20%, or about 15% by weight of the total weight of the pharmaceutical composition. In some embodiments, the pharmaceutical composition comprises about 20% by weight of microcrystalline cellulose.

In some embodiments, the pharmaceutical composition comprises a processing aid. In some embodiments, the processing aid is colloidal silicon dioxide. In the embodiment, the pharmaceutical composition comprises colloidal silicon dioxide between about 1% to about 2.5% by weight of the total weight of the pharmaceutical composition. In some embodiments, the pharmaceutical composition comprises colloidal silicon dioxide at about 1%, about 1.5%, about 2%, or about 2.5% by weight of the total weight of the pharmaceutical composition.

In some embodiments, the processing aid is magnesium stearate. In the embodiment, the pharmaceutical composition comprises magnesium stearate between about 0.5% to about 1.5% by weight of the total weight of the pharmaceutical composition. In some embodiments, the pharmaceutical composition comprises magnesium stearate at about 0.5%, about 0.8%, about 1.0%, about 1.2%, or about 1.5% by weight of the total weight of the pharmaceutical composition.

In some embodiments, the pharmaceutical composition comprises pre-gelatinized starch, colloidal silicon dioxide, and magnesium stearate at a weight ratio of 5:2:1.

In some embodiments, the pharmaceutical composition comprising Compound 1 or a pharmaceutically acceptable salt or polymorph thereof, is stored at controlled room temperature (20-25° C.).

In some embodiments, the pharmaceutical composition comprising Compound 1 or a pharmaceutically acceptable salt or polymorph thereof, is protected from light.

In some embodiments, the pharmaceutical composition has a friability and/or a disintegration time. Friability, as disclosed herein, is the tendency for a tablet to chip, crumble or break following compression. Friability testing is a laboratory technique to test the durability of tablets. This testing involves repeatedly dropping a sample of tablets over a fixed time, using a rotating wheel with a baffle. Friability is determined by the USP (United States Pharmacopeia) standard test for tablet friability. In some embodiments, the pharmaceutical composition has a friability of no more than about 0.5% weight loss of the tablet. In some embodiments, the pharmaceutical composition has a friability of no more than about 0.4% weight loss of the tablet. In some embodiments, the pharmaceutical composition has a friability of no more than about 0.3% weight loss of the tablet. In some embodiments, the pharmaceutical composition has a friability of no more than about 0.25% weight loss of the tablet.

Disintegration tests are used to test how a drug in pellet form will disintegrate in solution. These tests can be correlated with the in vitro breakdown of powdered compounds for quality control purposes. Disintegration is defined as that state in which no residue of the unit under test remains on the screen of the apparatus or, if a residue remains, it consists of fragments of disintegrated parts of tablets component parts such as insoluble coating of the tablets or of capsule shells, or of any melted fatty substance. This test is most often performed on products that have known absorption problems or known poor solubility. It is also performed on sustained or delayed release products such as enteric coated products. Dissolution testing can be carried out on either capsules or tablets. In some embodiments, the pharmaceutical composition has a dissolution time of no more than 15 minutes.

In some embodiments, the pharmaceutical composition further comprises hydroxypropyl cellulose. Hydroxypropyl cellulose is a derivative of cellulose with both water and organic solubility. It is often used as a pharmaceutical excipient. Hydroxypropyl cellulose can be used as a tablet binder, thickening agent, viscosity-increasing agent, a coating agent, and a film forming agent. In some embodiments, the pharmaceutical composition further comprises from about 1% to about 6% by weight of the table of hydroxypropyl cellulose. In some embodiments, the pharmaceutical composition further comprises from about 4% to about 5% by weight of the table of hydroxypropyl cellulose. In some embodiments, hydroxypropyl cellulose is present at about 4% weight of the tablet. In some embodiments, hydroxypropyl cellulose is present at about 5% weight of the tablet. In some embodiments, hydroxypropyl cellulose is present at about 6% weight of the tablet.

In some embodiments, the pharmaceutical composition has a tablet hardness and/or a tablet thickness. Tablet hardness testing, is a laboratory technique used by the pharmaceutical industry to determine the breaking point and structural integrity of a tablet and find out how it changes under conditions of storage, transportation, packaging and handling before usage. The breaking point of a tablet is based on its shape. In some embodiments, the table has a hardness of about 10 kPa. In some embodiments, the tablet has a thickness of about 4.5-5.0 mm. In some embodiments, the tablet has a thickness of about 4.65-4.85 mm.

In some other embodiments, the composition comprising Compound 1 or a pharmaceutically acceptable salt or polymorph thereof, is suitable for pediatric uses and can be taken by pediatric sickle cell anemia patients.

In some embodiments, the pharmaceutical composition comprising Compound 1 or a pharmaceutically acceptable salt or polymorph thereof, is taken with food. In some embodiments, the pharmaceutical composition, is taken after a meal. In some embodiments, the pharmaceutical composition, is taken without food.

Dosing

In some embodiments, the oral dosage ranges from about 0.001 to about 100 mg/kg body weight per day. In some embodiments, the oral dosage range is from about 0.01 to about 50 mg/kg body weight per day. In some embodiments, the oral dosage range is from about 0.05 to about 10 mg/kg body weight per day. Oral dosages are usually administered in one or more dosages, typically, one to three dosages per day. In some embodiments, the dose is administered once, twice, or three times a day. The exact dosage will depend upon the frequency and mode of administration, the gender, age, weight, and general health of the subject treated, the nature and severity of the condition treated and any concomitant diseases to be treated and other factors evident to those skilled in the art.

In some embodiments, Compound 1 or a pharmaceutically acceptable salt or polymorph thereof is administered to a subject in need thereof, at a dose of less than 6.0 mg/kg or less than about 4.0 mg/kg per body weight of the subject. In some embodiments, Compound 1 or a pharmaceutically acceptable salt or polymorph thereof, is administered at a dose of from about 0.1 mg/kg to about 6.0 mg/kg per body weight of the subject. For example, Compound 1 or a pharmaceutically acceptable salt or polymorph thereof, is administered at a dose of from about 0.3 to about 3.0 mg/kg, or from about 0.3 to about 1.0 mg/kg per body weight of the subject. The patient may have sickle cell disease. The patient may be an adult (>18 years old) or a child (<18 years old). In some embodiments, the patient receives Compound 1 or a pharmaceutically acceptable salt or polymorph thereof at a dose of around 0.3 mg/kg, around 0.2 mg/kg, around 0.1 mg/kg, or around 0.05 mg/kg per body weight of the subject. In some embodiments, the patient receives Compound 1 or a pharmaceutically acceptable salt or polymorph thereof, at about 1 mg/kg per body weight of the subject. In some embodiments, the patient receives Compound 1 or a pharmaceutically acceptable salt or polymorph thereof, at about 3 mg/kg per body weight of the subject. In some embodiments, the patient receives Compound 1 or a pharmaceutically acceptable salt or polymorph thereof, at about 6 mg/kg per body weight of the subject.

In some embodiments, the patient receives Compound 1 or a pharmaceutically acceptable salt or polymorph thereof, at about 0.1 mg/kg per body weight of the subject.

In some embodiments, the patient receives Compound 1 or a pharmaceutically acceptable salt or polymorph thereof, at about 0.3 mg/kg per body weight of the subject.

In some embodiments, the patient receives Compound 1 or a pharmaceutically acceptable salt or polymorph thereof, at about 0.5 mg/kg per body weight of the subject.

In some embodiments, the patient receives Compound 1 or a pharmaceutically acceptable salt or polymorph thereof, at about 1 mg/kg per body weight of the subject.

In some embodiments, the patient receives Compound 1 or a pharmaceutically acceptable salt or polymorph thereof, at about 5 mg/kg per body weight of the subject.

In some embodiments, the patient receives Compound 1 or a pharmaceutically acceptable salt or polymorph thereof, at about 10 mg/kg per body weight of the subject.

In some embodiments, Compound 1 or a pharmaceutically acceptable salt or polymorph thereof is administered to a patient in need thereof, at a flat dose of about 20 mg, about 50 mg, about 100 mg, about 200 mg, about 300 mg, about 400, about 500 mg, or about 600 mg per day. In some embodiments, Compound 1 or a pharmaceutically acceptable salt or polymorph thereof is administered to a patient at a dose of about 50 mg, about 100 mg, about 150 mg, about 200 mg, about 250 mg, about 300 mg, or about 350 mg. In some embodiments, Compound 1 or a pharmaceutically acceptable salt or polymorph thereof is administered at a dose of about 50 mg. In some embodiments, Compound 1 or a pharmaceutically acceptable salt or polymorph thereof is administered at a dose of about 100 mg. In some embodiments, Compound 1 or a pharmaceutically acceptable salt or polymorph thereof is administered at a dose of about 150 mg. In some embodiments, Compound 1 or a pharmaceutically acceptable salt or polymorph thereof is administered at a dose of about 200 mg. In some embodiments, Compound 1 or a pharmaceutically acceptable salt or polymorph thereof is administered at a dose of about 250 mg. In some embodiments, Compound 1 or a pharmaceutically acceptable salt or polymorph thereof is administered at a dose of about 300 mg. In some embodiments, Compound 1 or a pharmaceutically acceptable salt or polymorph thereof is administered at a dose of about 350 mg. In some embodiments, Compound 1 or a pharmaceutically acceptable salt or polymorph thereof is administered at a dose of about 400 mg.

In some embodiments of the pharmaceutical composition, Compound 1 is administered at a maximum dose per day or per dose. In some embodiments, a total combined dose of 1 g of Compound 1, or a pharmaceutically acceptable salt, solvate or polymorph thereof, is administered per day or per dose. In some embodiments, a total combined dose of 600 mg Compound 1, or a pharmaceutically acceptable salt, solvate or polymorph thereof, is administered per day or per dose. In some embodiments, a total combined dose of 500 mg Compound 1, or a pharmaceutically acceptable salt, solvate or polymorph thereof, is administered per day or per dose. In some embodiments, a total combined dose of 400 mg Compound 1, or a pharmaceutically acceptable salt, solvate or polymorph thereof, is administered per day or per dose. In some embodiments, a total combined dose of 300 mg Compound 1, or a pharmaceutically acceptable salt, solvate or polymorph thereof, is administered per day or per dose. In some embodiments, a total combined dose of 200 mg Compound 1, or a pharmaceutically acceptable salt, solvate or polymorph thereof, is administered per day or per dose. In some embodiments, Compound 1 or a pharmaceutically acceptable salt or polymorph thereof, is administered to a patient, wherein Compound 1 or a pharmaceutically acceptable salt or polymorph thereof is administered once a day. In some embodiments, the pharmaceutical composition is administered twice a day.

In some embodiments, Compound 1 or a pharmaceutically acceptable salt or polymorph thereof is administered to a patient, wherein Compound 1 or a pharmaceutically acceptable salt or polymorph thereof is administered once a day with food. It has been found that food can dramatically reduce the adverse event profile. The incidence and severity of the side effects, such as nausea, emesis and headache, can be reduced when Compound 1 or a pharmaceutically acceptable salt or polymorph thereof, is taken with food.

In some embodiments, Compound 1 or a pharmaceutically acceptable salt or polymorph thereof, is administered to a patient, wherein Compound 1 or a pharmaceutically acceptable salt or polymorph thereof is administered once a day for at least 7 days, 10 days, 2 weeks, 3 weeks, 4 weeks, 1 month, 2 months, 3 months, 4 months, 6 months, 7 months, 8 months, 9 months, 10 months, 11 months, a year, 1.5 years, or 2 years. In some embodiments, the patient is treated for 3 months. In some embodiments, the patient is treated for 6 months. In some embodiments, the patient is treated for 1 year. In some embodiments, the patient is treated for 1.5 years. In some embodiments, the patient is treated for 2 years, 3 years, 4 years, 5 years, over 5 years, or the duration of life.

In some embodiments, the pharmaceutical compositions are presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

Combination Therapies

In one embodiment, the pharmaceutical composition comprising compounds of the present disclosure is used in combination with an additional active agent, such as Hydroxyurea (HU). The compounds of the present disclosure and the additional active agent may be administered simultaneously, sequentially, or at any order. The compounds of the present disclosure and the additional active agent may be administered at different dosages, with different dosing frequencies, or via different routes, whichever is suitable.

The term "administered simultaneously", as used herein, is not specifically restricted and means that the compounds of the present disclosure and the additional active agent are substantially administered at the same time, e.g. as a mixture or in immediate subsequent sequence.

The term "administered sequentially", as used herein, is not specifically restricted and means that the compounds of the present disclosure and the additional active agent are not administered at the same time but one after the other, or in groups, with a specific time interval between administrations. The time interval may be the same or different between the respective administrations of the compounds of the present disclosure and the additional active agent and may be selected, for example, from the range of 2 minutes to 96 hours, 1 to 7 days or one, two, or three weeks. Generally, the time interval between the administrations may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

The molar ratio of the compounds of the present disclosure and the additional active agent is not particularly restricted. For example, when the compounds of the present disclosure and one additional active agent are combined in a composition, the molar ratio of them may be in the range of 1:500 to 500:1, or of 1:100 to 100:1, or of 1:50 to 50:1, or of 1:20 to 20:1, or of 1:5 to 5:1, or 1:1. Similar molar ratios apply when the compounds of the present disclosure and two or more other active agents are combined in a composition. The compounds of the present disclosure compounds of the present disclosure may comprise a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% of the composition.

Methods of Using Compounds of the Disclosure

PDE9 is expressed specifically in the human haematopoietic system including neutrophils, reticulocytes erythroid and erythroleukaemic cells. Furthermore, SCD patients exhibit a marked and significant elevation of PDE9 expression in reticulocytes and neutrophils compared to healthy individuals (Almeida et al., *Br J Haematol.* 2008 September; 142(5), 836). Evidence additionally demonstrates a link between PDE9 and cell adhesion since pharmacologic PDE9 inhibition ameliorates the increased adhesive properties of SCD neutrophils (Miguel et al., *Inflamm Res.* 2011 July; 60(7), 633). The mechanism by which PDE9 inhibition decreases cell adhesion has been shown to be mediated by increased cGMP and decreased endothelial adhesion molecule expression. Importantly, in an animal model of SCD, the PDE9 inhibitor-mediated decrease in cell adhesion had the functional effect of increased cell survival. In addition to demonstrating decreased cell adhesion comparable to HU, PDE9 inhibition resulted in increased fetal non-sickled haemoglobin (HbF) production, which reduced the cellular concentration of abnormal haemoglobin (HbS) within red blood cells (RBCs) resulting in less polymerization of the abnormal haemoglobin and its associated sequelae. The importance of increasing HbF in treating SCD is evidenced by results of large studies like the Cooperative Study of Sickle Cell Disease, as well as studies in a variety of patient cohorts outside of the United States, showing that HbF is among the most important modifiers of this disease (Alsultan et al., *Am J Hematol.* 2013, 88(6), 531) as well as data showing that modifiers of HbF improve other hematological parameters (Akinsheye, *Blood,* 2011, 118(1):19). Finally, Almeida and colleagues demonstrated that treatment with HU combined with PDE9 inhibition in a mouse model of SCD leads to an additional beneficial amplification of the cGMP elevating effects of HU (Almeida et al., *Blood.* 2012 October; 120(14), 2879). In conclusion, PDE9 inhibition can modulate both the expression of fetal haemoglobin production as well as decrease cell adhesion, both mechanisms key for the treatment of SCD.

PDE9 inhibitors of the present disclosure and hydroxyurea (HU) act through different mechanisms. HU increases nitric oxide (NO) levels, which activate soluble guanylyl cyclase (sGC) to generate cGMP. PDE9 inhibitors of the present disclosure block the degradation of cGMP by inhibiting PDE9 enzymatic activity, thus elevating cGMP levels. In erythroid lineages, cGMP binds to protein kinase G (PKG) and signals synthesis of fetal gamma globin and ultimately production of HbF. In hematopoietic cells where PDE9 expression is high, the direct inhibition of PDE9 activity increases cGMP levels, which promotes decreased leucocyte adhesion.

One aspect of the present disclosure provides methods of using PDE9 inhibitors of the present disclosure and pharmaceutical compositions comprising PDE9 inhibitors of the present disclosure.

PDE9 inhibitors of the present disclosure may be used to treat sickle cell disease or any disease and/or symptom related to sickle cell disease, such as anemia, sickle-hemoglobin C disease (SC), vaso-occlusive crisis, attacks of pain (sickle cell crisis), splenic sequestration crisis, acute chest syndrome, aplastic crisis, hemolytic crisis, long-term pain, bacterial infections, and stroke.

In one embodiment, PDE9 inhibitors of the present disclosure are used to increase hemoglobin levels in the subject.

In another embodiment, PDE9 inhibitors of the present disclosure are used to increase cGMP levels in a cell or in the plasma of a subject, wherein the subject has sickle cell disease. The cell may be, but not limited to, red blood cells and/or white blood cells. The cGMP level may be increased by at least 50%, at least 100%, or at least 150%. In some embodiments, the cGMP level may be increased at least 2 times, 3 times, 4 times, 5 times, 10 times, 15 times, 20 times, or 25 times.

In another embodiment, PDE9 inhibitors of the present disclosure are used to increase fetal hemoglobin (HbF) positive red blood cell number in a subject, wherein the subject has sickle cell disease. The HbF positive red blood cell number is increased by at least 50%, at least 100%, or at least 150%. In some embodiments, the HbF positive red blood cell number is increased by at least 2 times, 3 times, 4 times, 5 times, 10 times, 15 times, 20 times, or 25 times.

In another embodiment, PDE9 inhibitors of the present disclosure are used to reduce sickle red blood cell percentage (% sickle RBC), stasis percentage (% stasis), total bilirubin, or total leucocyte count in a subject, wherein the subject has sickle cell disease. The % sickle RBC, % stasis, total bilirubin, total leucocyte count or spleen weight is decreased by at least 10%, 20%, 30%, 40%, 50%, 60% or 70%.

cGMP level may be measured with any suitable method in the art, such as enzyme immunoassay.

HbF positive cells, as used herein, means red blood cells with HbF. HbF positive cells may be measured from a blood sample with any suitable method in the art, such as electrophoresis and/or colorimetric methods.

Sickle red blood cells, sickled red blood cells, as used herein, means red blood cells with a crescent or sickle shape. % sickle red blood cell may be measured from a blood sample with any suitable method in the art.

Stasis or microvascular stasis, as used herein, is serious slowing, or complete cessation, of blood or lymph flow through vessels. % stasis is the number of static (no flow) venules divided by the number of flowing venules times 100. % stasis may be measured with any suitable method in the art.

Total bilirubin, as used herein, means both unconjugated and conjugated bilirubin. Total bilirubin levels may be measured from a blood sample with any suitable method in the art.

Total leucocyte count or total white blood cell count, as used herein, is a blood test that measures the number of white blood cells in the body. It may be measured from a blood sample with any suitable method in the art.

Another aspect of the present disclosure provides methods of using a PDE9 inhibitor of the present disclosure in combination with at least one other active agent. They may be administered simultaneously or sequentially. They may be present as a mixture for simultaneous administration, or may each be present in separate containers for sequential administration.

The term "simultaneous administration", as used herein, is not specifically restricted and means that the PDE9 inhibitor of the present disclosure and the at least one other active agent are substantially administered at the same time, e.g. as a mixture or in immediate subsequent sequence.

The term "sequential administration", as used herein, is not specifically restricted and means that the PDE9 inhibitor of the present disclosure and the at least one other active agent are not administered at the same time but one after the other, or in groups, with a specific time interval between administrations. The time interval may be the same or different between the respective administrations of PDE9 inhibitor of the present disclosure and the at least one other active agent and may be selected, for example, from the range of 2 minutes to 96 hours, 1 to 7 days or one, two or three weeks. Generally, the time interval between the administrations may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

The molar ratio of the PDE9 inhibitor of the present disclosure and the at least one other active agent is not particularly restricted. For example, when a PDE9 inhibitor of the present disclosure and one other active agent are combined in a composition, the molar ratio of them may be in the range of 1:500 to 500:1, or of 1:100 to 100:1, or of 1:50 to 50:1, or of 1:20 to 20:1, or of 1:5 to 5:1, or 1:1. Similar molar ratios apply when a PDE9 inhibitor of the present disclosure and two or more other active agents are combined in a composition. The PDE9 inhibitor of the present disclosure may comprise a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% of the composition.

The other active agent may be a different PDE9 inhibitor of the present disclosure or HU. The other active agent may also be an antibiotic agent such as penicillin, a nonsteroidal anti-inflammatory drug (NSAIDS) such as diclofenac or naproxen, a pain relief medication such as opioid, or folic acid.

Yet another aspect of the present disclosure provides methods of using a PDE9 inhibitor of the present disclosure in combination with at least one other therapy, such as but not limited to blood transfusion, bone marrow transplant, or gene therapy.

Kits and Devices

The disclosure provides a variety of kits and devices for conveniently and/or effectively carrying out methods of the present disclosure. Typically, kits will comprise sufficient amounts and/or numbers of components to allow a user to perform multiple treatments of a subject(s) and/or to perform multiple experiments.

In one embodiment, the present disclosure provides kits for treating sickle cell disease, comprising a PDE9 inhibitor compound of the present disclosure or a combination of PDE9 inhibitor compounds of the present disclosure, optionally in combination with any other active agents, such as HU, an antibiotic agent such as penicillin, a nonsteroidal anti-inflammatory drug (NSAIDS) such as diclofenac or naproxen, a pain relief medication such as opioid, or folic acid.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of PDE9 inhibitor compounds in the buffer solution over a period of time and/or under a variety of conditions.

The present disclosure provides for devices that may incorporate PDE9 inhibitor compounds of the present disclosure. These devices contain in a stable pharmaceutical formulation available to be immediately delivered to a subject in need thereof, such as a human patient with sickle cell disease.

Non-limiting examples of the devices include a pump, a catheter, a needle, a transdermal patch, a pressurized olfactory delivery device, iontophoresis devices, multi-layered microfluidic devices. The devices may be employed to deliver PDE9 inhibitor compounds of the present disclosure according to single, multi- or split-dosing regiments. The devices may be employed to deliver PDE9 inhibitor compounds of the present disclosure across biological tissue, intradermal, subcutaneously, or intramuscularly. More examples of devices suitable for delivering PDE9 inhibitor compounds include but not limited to a medical device for intravesical drug delivery disclosed in International Publication WO 2014036555, a glass bottle made of type I glass disclosed in US Publication No. 20080108697, a drug-eluting device comprising a film made of a degradable polymer and an active agent as disclosed in US Publication No. 20140308336, an infusion device having an injection micro-pump, or a container containing a pharmaceutically stable preparation of an active agent as disclosed in U.S. Pat. No. 5,716,988, an implantable device comprising a reservoir and a channeled member in fluid communication with the reservoir as disclosed in International Publication WO 2015023557, a hollow-fiber-based biocompatible drug delivery device with one or more layers as disclosed in US Publication No. 20090220612, an implantable device for drug delivery including an elongated, flexible device having a housing defining a reservoir that contains a drug in solid or semi-solid form as disclosed in International Publication WO 2013170069, a bioresorbable implant device disclosed in U.S. Pat. No. 7,326,421, contents of each of which are incorporated herein by reference in their entirety.

Definitions

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of"

or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to amelioration of a disease or disorder, or at least one sign or symptom thereof "Treatment" or "treating" can refer to reducing the progression of a disease or disorder, as determined by, e.g., stabilization of at least one sign or symptom or a reduction in the rate of progression as determined by a reduction in the rate of progression of at least one sign or symptom. In another embodiment, "treatment" or "treating" refers to delaying the onset of a disease or disorder.

As used herein, "prevention" or "preventing" refers to a reduction of the risk of acquiring or having a sign or symptom a given disease or disorder, i.e., prophylactic treatment.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, e.g., ameliorates at least one sign or symptom of the disorder. In various embodiments, the disease or disorder is a cancer.

A dash ("-") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

All numerical ranges herein include all numerical values and ranges of all numerical values within the recited range of numerical values. As a non-limiting example, $(C_1-C_6)$ alkyls also include any one of $C_1$, $C_2$, $C_3$, $C_4$, $C_5$, $C_6$, $(C_1-C_2)$, $(C_1-C_3)$, $(C_1-C_4)$, $(C_1-C_5)$, $(C_2-C_3)$, $(C_2-C_4)$, $(C_2-C_5)$, $(C_2-C_6)$, $(C_3-C_4)$, $(C_3-C_5)$, $(C_3-C_6)$, $(C_4-C_5)$, $(C_4-C_6)$, and $(C_5-C_6)$ alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

LIST OF ABBREVIATIONS AND TERMS $^1$H-NMR: Proton Nuclear Magnetic Resonance spectroscopy
ADME: Absorption, Distribution, Metabolism, and Excretion
AE: Adverse event
$AUC_{0-24}$: area under the concentration-time curve from time 0 to 24 hours postdose
BBB: blood-brain barrier
$C_{max}$: maximum plasma concentration
cGMP: cyclic guanosine monophosphate
DMSO: dimethyl sulfoxide
DSFC: dorsal skin-fold chambers
F cells: blood cells with fetal haemoglobin
FIH: first in human
FTIR: Fourier transform infrared spectroscopy
GC: gas chromatography
HBB: hemoglobin subunit beta
HbF: fetal hemoglobin
HBG: gamma-globin gene
HbS: sickle hemoglobin
hERG: human ether-á-go-go related gene
HPLC: high-performance liquid chromatography
HU: hydroxyurea
IC: inhibitory concentration
$IC_{50}$: a half minimal inhibitory concentration
ICAM-1: intercellular adhesion molecule-1
ICH: International Conference on Harmonization
ICP-MS: inductively coupled plasma mass spectroscopy
IV: intravenous MAD: multiple-ascending dose
MTD: maximum tolerated dose
NO: nitric oxide
NOAEL: no-observed-adverse-effect level
PD: pharmacodynamic
PDE9: phosphodiester-9
PEG polyethylene glycol
PIC: Powder in capsule
PK: pharmacokinetic(s)
PKG: protein kinase G
RBC: red blood cell
RH: relative humidity
SCD: sickle cell disease
SD: standard deviation
SEM: standard error of the mean
sGC: soluble guanylyl cyclase
$t_{1/2}$: half-life
TK: Toxicokinetic
$T_{max}$: time of maximum concentration
VOC: vaso-occlusive crisis
WBC: white blood cell
w/w %: weight/weight percent

EXAMPLES

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

Example 1. Synthesis and Formulation of Compound 1

Compound 1 is an enantiomer of 6-[4-methyl-1-(pyrimidin-2-ylmethyl)pyrrolidin-3-yl]-3-tetrahydropyran-4-yl-7H-imidazo[1,5-a]pyrazin-8-one disclosed in WO 2013/053690. Compound 1 may be prepared from chiral-selective purification from 6-[4-methyl-1-(pyrimidin-2-ylmethyl)pyrrolidin-3-yl]-3-tetrahydropyran-4-yl-7H-imidazo[1,5-a]pyrazin-8-one prepared according to the method disclosed in WO 2013/053690, the contents of which are incorporated herein by reference in their entirety. Compound 1 may also be prepared with the method disclosed in WO 2017/005786, the contents of which are incorporated herein by reference in their entirety.

Compound 1

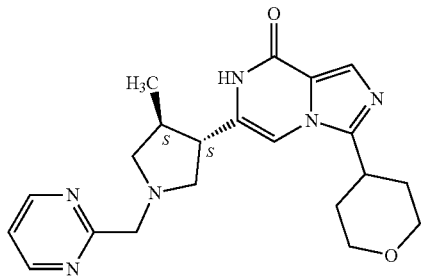

Compound 1 drug product to be used in ongoing clinical development is an immediate release tablet. The coating is may be used to assure uniformity of appearance across different tablet strengths and with the placebo.

Earlier clinical studies were performed with Compound 1 drug substance directly filled into opaque white gelatin capsules (Powder in Capsule, PIC) with no excipients or processing aids. An excipient-blended tablet form of the drug product for oral administration has been developed, as this allowed for scale-up of the manufacturing process and assurance of content uniformity. These tablets were tested for defined limits for purity, potency, dissolution, total aerobic microbial count, as well as total yeast and mold count. In addition, tests for specified microorganisms were performed.

Each tablet comprises 20 mg, 50 mg, 100 mg, or 200 mg of Compound 1 drug substance (the monohydrate of the API) or placebo. A representative tablet composition is shown below in Table 1.

TABLE 1

| Compound 1 50 mg coated tablets | |
|---|---|
| Component | Weight/Unit (mg) |
| Tablet Blend | |
| Compound 1 Drug Substance | 50.0 |
| Microcrystalline Cellulose | 318.0 |
| Pre-gelatinized Starch | 20.0 |
| Colloidal Silicon Dioxide | 8.0 |
| Magnesium Stearate | 4.0 |
| Tablet Core Total | 400.0 |
| Coating Solution | |
| Opadry II White Film Coating | 40.0 |
| Purified Water | — |
| Final | 440.0 |

Purified water is removed during processing.

All tablets were configured such that the target weight of the core tablets was 400 mg, and the target weight of the coated tablet was 440 mg. To accomplish this, the amounts of Compound 1 and Microcyrstalline Cellulose were adjusted accordingly. All other excipient amounts remained constant.

Description of Manufacturing Process and Process Controls

The manufacture of the coated tablets follows common procedures for blending, tablet compaction, and coating.

Roller Compaction of Drug Substance

Compound 1 drug substance was first processed by roller compaction to achieve a more uniform intermediate that is suitable for further blending and processing. A defined amount of API was passed through a roller compactor at 200-300 PSI and a roller speed of 4.0 RPM. The roller compacted material was passed through a 20-mesh screen to obtain a uniform particle size. The compacted and screened API was stored in double lined polyethylene bags pending use in tablet manufacturing.

Blending of Roller Compacted Drug Substance with Excipients

A defined amount of the roller compacted API was mixed with the defined excipients (excluding the coating solution) using a 16 qt. V-shell Blender. Blending was performed in a manner such that not less than 300 revolutions of the blender were completed in the defined period. Samples were taken from multiple locations in the V-Shell Blender to verify the blend uniformity.

Blended material was stored in a suitable HDPE container within double lined polyethylene bags pending further processing.

Tableting

Tablet manufacturing was performed in a gravity fed tablet press with 11 mm upper and lower plain-faced tablet punches. The tablet press was adjusted to meet predetermined specifications for tablet weight, hardness, thickness, friability, and disintegration, as defined below. All core tablets are screened through a metal detector and de-dusted prior to film coating.

Film Coating

A uniform coating mixture was prepared by mixing the defined amount of Opadry II White in Purified Water and mixing the suspension for no less than 45 minutes. Tablets were loaded on to the pan coating equipment and preheated to 43° C. prior to initiation of the coating operations. The preheated tablets were then coated in a 15-inch coating pan rotating at 10-15 RPM. The spray rate of the coating suspension was controlled at 10 grams per minute, and inlet air temperature maintained between 40-60° C.

Tablets were sampled at defined intervals and weighed to determine if the desired target weight gain (10%) has been met. Once coating is completed the coated tablets were allowed to cool to ≤30° C.

Bulk Packaging

Coated tablets were sampled for release testing and then transferred into a HDPE container double lined with double lined polyethylene bags.

Clinical Packaging

Packaging of tablets for clinical trials was performed, including inkjet labeling of each container with the batch number to ensure identification. Thirty-three (33) tablets were filled into each 60 cc round white HDPE bottle by manual count. The count was verified by a second person before each bottle was filled. Following filling each bottle was manually closed with a 33-mm white polypropylene child resistant cap, and induction sealed.

Example 2. Development of 300 mg Tablet

Development activities for the 300 mg tablet have shown that the addition of Hydroxypropyl Cellulose (HPC-SSL-SFP) and elevation of Microcrystalline Cellulose (Avicel PH200) percent level resulted in acceptable results of an increased tablet hardness and decreased loss during friability testing. However, the addition of HPC has increased the mean disintegration time from less than one minute to approximately 37 minutes. Multiple percent levels of HPC-SSL-SFP were evaluated in the formulation for the 300 mg tablet. The formulations being evaluated are shown below in Table 2.

TABLE 2

Optimization of HPC-SSL-SFP Percent Levels Utilized in Formulation.

| | mg/unit | | | | |
|---|---|---|---|---|---|
| Component | Formulation A 0.5% HPC | Formulation B 1.0% HPC | Formulation C 1.5% HPC | Formulation D 2.0% HPC | Formulation E 2.5% HPC |
| Compound 1 Drug Substance, Densified | 300.0 | 300.0 | 300.0 | 300.0 | 300.0 |
| Microcrystalline Cellulose NF/EP (Avicel PH200) | 84.30 | 82.20 | 80.10 | 78.00 | 75.90 |
| Pre-Gelatinized Starch NF/EP (Starch 1500) | 21.00 | 21.00 | 21.00 | 21.00 | 21.00 |
| Hydroxypropyl Cellulose (HPC-SSL-SFP) | 2.10 | 4.20 | 6.30 | 8.40 | 10.50 |
| Colloidal Silicon Dioxide, NF/EP (Cab-O-Sil) | 8.40 | 8.40 | 8.40 | 8.40 | 8.40 |
| Magnesium Stearate, NF/EP (non-bovine Hyqual) | 4.20 | 4.20 | 4.20 | 4.20 | 4.20 |
| Total Weight | 420.0 | 420.0 | 420.0 | 420.0 | 420.0 |

Multiple formulations of different percent levels of Hydroxypropyl Cellulose (HPC-SSL-SFP) were evaluated to determine the formulation that yielded acceptable results. The formulation utilized for the development of the 300 mg film-coated tablets, is shown below in Table 3.

TABLE 3

Formulation for 300 mg Film-Coated Tablets

| Ingredient | Percent Weight/Weight | Amount per Tablet (mg) |
|---|---|---|
| Compound 1 Drug Substance Densified | 71.4 | 300.0 |
| Microcrystalline Cellulose, NF/EP (Avicel PH 200) | 20.1 | 84.3 |
| Hydroxypropyl Cellulose (HPC-SSL-SFP) | 0.5 | 2.1 |
| Pre-gelatinized starch NF/EP (Starch 1500) | 5.0 | 21.0 |
| Colloidal Silicon Dioxide, NF/EP (Cab-O-Sil) | 2.0 | 8.4 |
| Magnesium Stearate, NF/EP (non-bovine Hyqual) | 1.0 | 4.2 |
| Total Core Tablet | 100.0 | 420.0 |
| Film-Coating | | |
| Opadry II, 85F18422, White | 4.8 | 20.0 |
| Total Coated Tablet | 104.8 | 440.0 |

Blending/Granulation

The excipients for development were record for a batch size of 2,380 tablets. Compound 1 drug substance was roller compacted. Compound 1 and all excipients were screened through a 20-mesh hand screen in the following order: 1) Compound 1 Drug Substance; 2) Pre-gelatinized Starch (Starch 1500); 3) Colloidal Silicon Dioxide (Cab-O-Sil); and 4) Microcrystalline Cellulose (Avicel PH200).

Once the target weight was achieved, a hardness profile (tablet hardness vs. disintegration time) was established and samples were collected. Each sample was used to execute tablet physical testing to include weight, hardness, thickness, disintegration, and friability.

In-Process Guidelines

Tablet Thickness Range: 4.65-4.85 mm.
Tablet Hardness Target: 10 kP.
Friability (USP Friability): no more than 0.3%, no capping.
Disintegration (per USP): All tablets completely disintegrate in no more than 15 minutes.

Coating

Tablets from development batch was coated at target conditions to evaluate the core tablet ability to withstand pan coating. Prior to charging the tablets into the coating pan, the pan was sprayed with the Opadry II, 85F18422, White and was allowed to dry. Operators monitored the spraying and drying process to ensure no flaking of the coating occurred. This created a thin layer of coating to prevent tablet defects caused by the coating pan such as scuffing. The tablets were coated to a 4.8% weight gain with Opadry II, 85F18422, White.

Results and Discussion

The goal of the development activities was to develop a formulation for the Compound 1 tablet which contained an optimal percent level of Hydroxypropyl Cellulose (HPC-SSL-SFP), yielding acceptable results. The formulation utilized was to produce a tablet with acceptable hardness, thickness, friability, and disintegration results. The tablets of each formulation were tested for hardness, thickness, friability, and disintegration. Target Results: (1) Thickness: 4.50-4.80 mm, (2) Friability: ≤0.3% loss, (3) Disintegration: ≤15 minutes, and (4) Hardness of about 10 kPa. Friability, disintegration and hardness were tested to USP Compounding standards (United States Pharmacopeia and National Formulary are recognized standards in testing).

Feasibility Batch with 0.5% HPC

The first formulation evaluated contained 0.5% Hydroxypropyl Cellulose (HPC-SSL-SFP), this formulation is shown below in Table 4.

TABLE 4

Formulation of Compound 1 300 mg tablets (0.5% HPC)

| Ingredient | Weight per Tablet (mg) |
|---|---|
| Compound 1 Drug Substance, Densified | 300.0 |
| Microcrystalline Cellulose (Avicel PH 200) | 84.3 |
| Hydroxypropyl Cellulose (HPC-SSL-SFP) | 2.1 |
| Pre-gelatinized Starch (Starch 1500) | 21.0 |
| Colloidal Silicon Dioxide (Cab-O-Sil) | 8.4 |
| Magnesium Stearate (non-bovine Hyqual) | 4.2 |
| Total Weight | 420.0 |

The tablets were to be prepared with a target fill weight of 420.0 mg, a thickness range of 4.50 mm-4.80 mm.

In order to test disintegration time, the tablets were submerged in water continuously until 6 tablets were completely disintegrated, the results are shown below in Table 5.

TABLE 5

Disintegration Time

| Tablet | Disintegration Time (mm:ss) | Compression Pressure (psi) |
|---|---|---|
| 1 | 03:24 | 2000 |
| 2 | 03:57 | 2000 |
| 3 | 06:40 | 2000 |
| 4 | 09:21 | 2600 |
| 5 | 12:40 | 2600 |
| 6 | 12:40 | 2600 |

The goal was to have all tablets completely disintegrate in 15 minutes or less. According to the data in Table 5 all tablets completely disintegrated in less than 15 minutes, meeting the goal time. The remaining tablet blend was compressed, using the target fill weight of 420.0 mg.

Another physical test performed was friability. The friability examines the tablets tendency for a tablet to chip, crumble or break following compression. The acceptance criteria for the batchs was a percent loss of 0.3% or less. The data collected during friability is shown below in Table 6.

TABLE 6

Friability

| Weight Before (g) | Weight After(g) | Loss | % Loss | # of Caps |
|---|---|---|---|---|
| 6.7378 | 6.7208 | 0.017 | 0.25 | 0 |

The 0.5% Hydroxypropyl Cellulose (HPC-SSL-SFP) percent level yielded results meeting the acceptance criterions provided in the batch record.

Feasibility Batch with 1.5% HPC

A tablet using the formulation containing 1.5% Hydroxypropyl Cellulose (HPC-SSL-SFP) was compressed, physical testing was conducted on these tablets to see if they too yielded acceptable results. The formulation is shown below in Table 7.

TABLE 7

Formulation of Compound 1, 300 mg tablets (1.5% HPC)

| Ingredient | Weight per Tablet (mg) |
|---|---|
| Compound 1 Drug Substance, Densified | 300.0 |
| Microcrystalline Cellulose (Avicel PH 200) | 80.10 |
| Hydroxypropyl Cellulose (HPC-SSL-SFP) | 6.30 |
| Pre-gelatinized Starch (Starch 1500) | 21.0 |
| Colloidal Silicon Dioxide (Cab-O-Sil) | 8.4 |
| Magnesium Stearate (non-bovine Hyqual) | 4.2 |
| Total Weight | 420.0 |

The tablets were submerged in water continuously until 3 tablets were completely disintegrated. The results are shown in Table 8.

TABLE 8

Disintegration Time

| Tablet | Disintegration Time (mm:ss) |
|---|---|
| 1 | 15:19 |
| 2 | 15:28 |
| 3 | 16:57 |

The disintegration times all exceeded the acceptance criteria of 15 minutes indicating failing results for disintegration. The increased disintegration time is caused by the increased Hydroxypropyl Cellulose (HPC-SSL-SPF) level. It can be noted that the loss after friability is less than 0.3%.

After physical testing concluded, and the tablets were film coated to a weight gain of approximately 4.8% w/w. After comparing the results from the physical tests conducted on each of the formulations, it was determined that the Compound 1, 300 mg tablet (0.5% HPC) yielded the acceptable results for the tablet.

Example 3. Compound 1 Reduces White Cell Adhesion and Activation

Polymorphic mononuclear cells (PMN), particularly neutrophils, play a critical role in pathogenesis of sickle cell disease (SCD) and activated neutrophils have been shown to be more adhesive to each other, platelets and the vascular endothelium. Recently several drugs targeting white cell binding to endothelial cells, have been advancing in clinical studies in patients. Compound 1 is able to increase expression of fetal hemoglobin in patient derived cells and murine models of SCD and reduce vessel occlusion in SCD murine models. In this Example, the ability of Compound 1 to reduce the adhesive properties of neutrophils from SCD patients and reduce sE-Selectin (sE-Sel) and markers of PMN activation in murine SCD models was studied.

Endothelial E-selectin (E-Sel) slows leukocyte rolling, which is followed by stationary adhesion and transmigration of activated leukocytes. Plasma levels of sE-Sel, produced by the enzymatic cleavage of the extracellular domains of E-Sel, are increased in SCD patients and this may be mediated by its interaction with leukocytes. In the Townes mouse model, plasma sE-Sel is increased 144% (139 mg/ml) over levels seen in control mice (57 mg/ml). This was reduced significantly in Townes mice treated with Compound 1, where plasma sE-Sel levels were elevated by only 61% over control mice (92 mg/ml).

Figure 2:
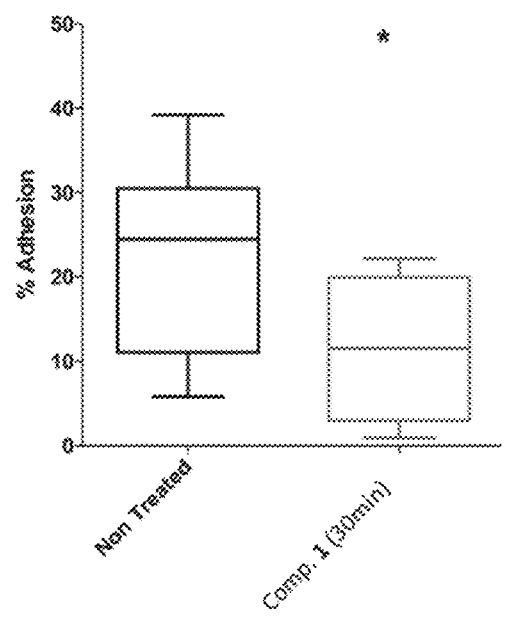
FIG. 2 shows Compound 1 reduces adhesion of SCD patient neutrophils to endothelial cell lined microfluidic chamber in vitro.
Figure 3:
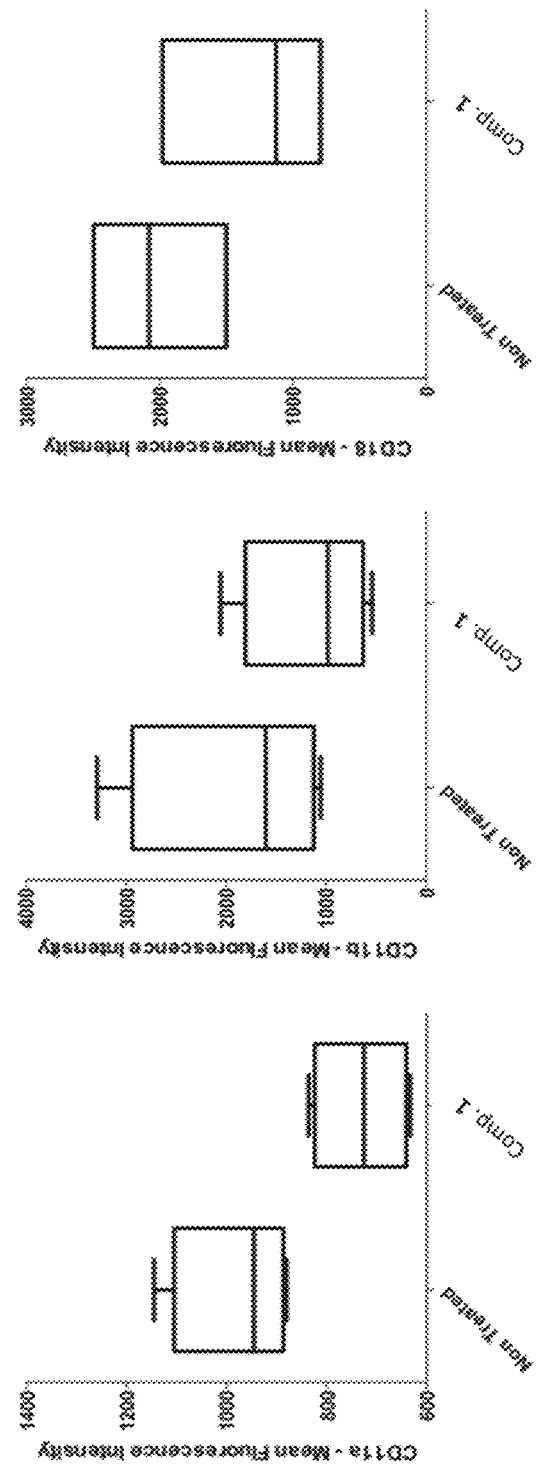
FIG. 3 shows Compound 1 reduces expression of CD11a, CD11b and CD18 integrins on SCD patient neutrophils.
Figure 5:
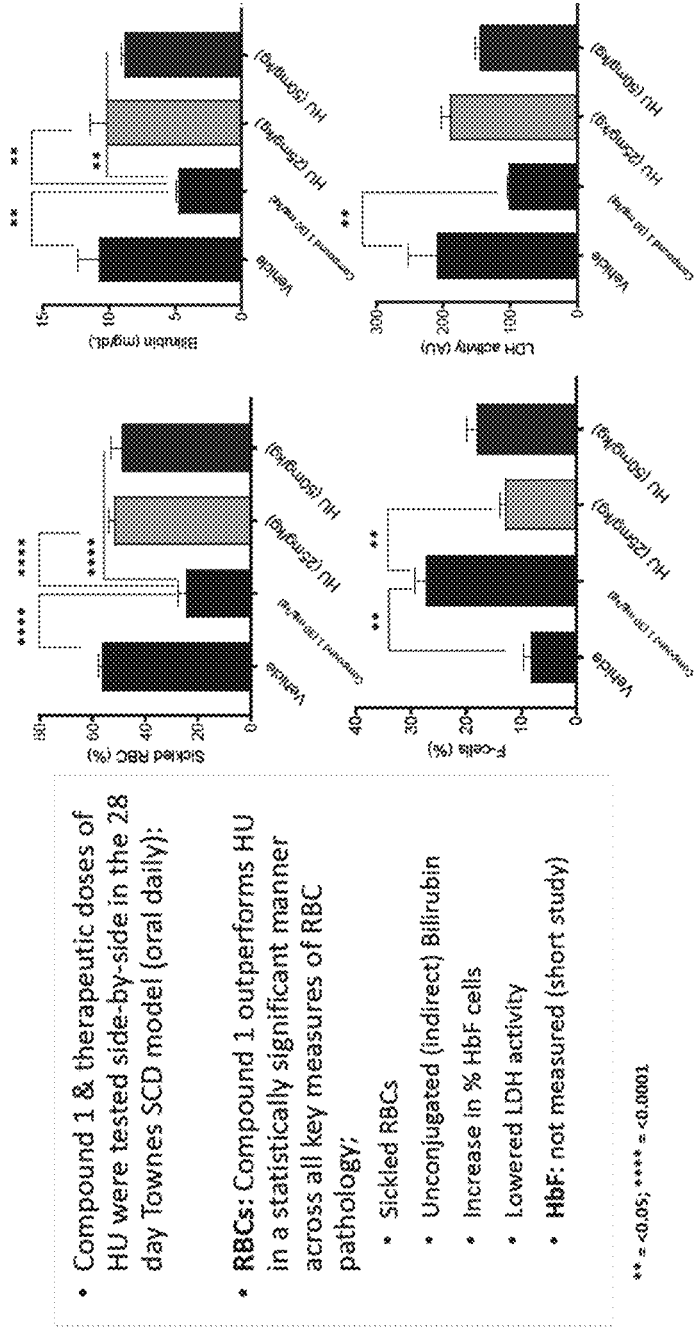
FIG. 5 shows the outcome of studies in the Townes SCD Model comparing Compound 1 (30 mg/kg).
Figure 6:
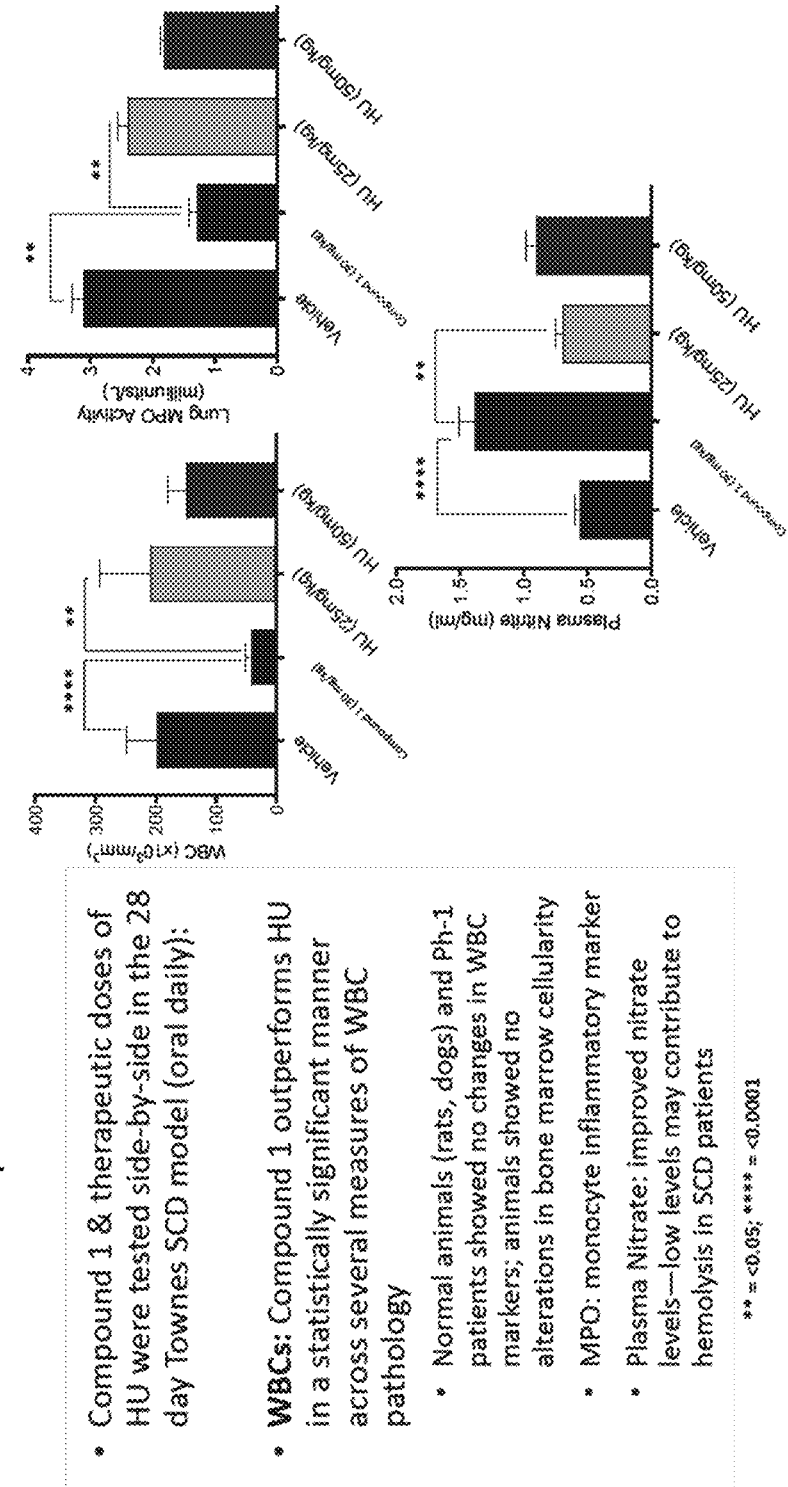
FIG. 6 shows the outcome of studies in the Townes SCD Model comparing Compound 1 (30 mg/kg).
Figure 7:
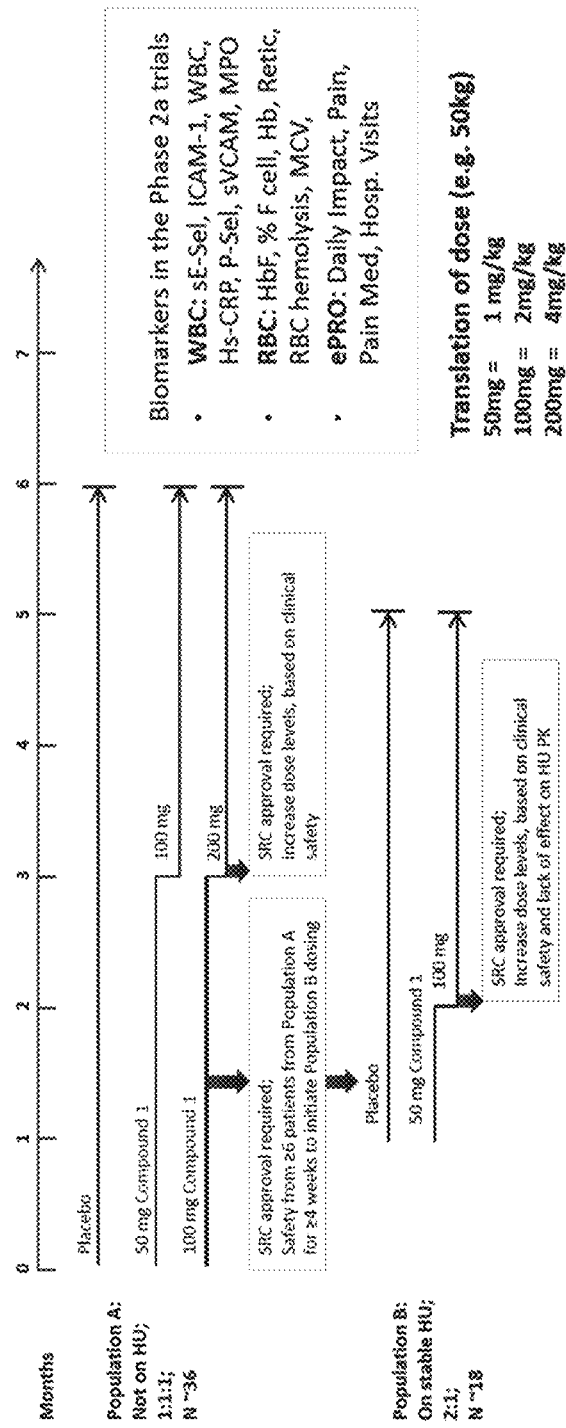
FIG. 7 illustrates a clinical study design for Compound 1.

It was found that Compound 1 reduced circulating levels of PMNs in SCD models, but not in long term studies in healthy animals. This appears to be accompanied by a Compound 1-mediated reduction in disease specific cell activation including 67% lower levels of myeloid derived myeloperoxidase (MPO) and 26% lower levels of neutrophil derived arginase in the lung (FIG. 1). Using a previously described in vitro adhesion assay mimicking blood flow, where activated endothelial cells HMEC-1 line the inner surface of microchannels, perfused whole blood samples from SS (the most common form of sickle cell) patients showed that neutrophils aggregate and bind to the endothelial monolayer. This was quantified by real time monitoring of the green florescent patches in the mircochannel, as neutrophils are labeled by a specific Alexa Fluor® 488-conjugated antibody before the perfusion step. Untreated, patient neutrophils showed a significant amount of adhesion to activated HMEC-1. When added to blood samples prior to the perfusion step, Compound 1 reduced adhesions significantly and in a dose dependent manner. The inhibitory effect was initiated as early as 15 min of incubation, with the most potent inhibition of adhesion observed for 30 min incubation with 30 µM of Compound 1. Under these conditions, adhesion was reduced an average of 54% (p=0.03) (FIG. 2). Mechanistically, not willing to be bound by any theory, Compound 1 may target the stationary adhesion step of neutrophils as it lowered expression levels of key neutrophil integrins including CD11a [reduced 23% (p=0.002)], CD11b [reduced 39% (ns)) and CD18 [reduced 47% (p=0.03)) (FIG. 3).

Together, these data indicate a role for Compound 1 in reducing PBMCs mediated pathology in SCD by targeting the abnormal adhesion of neutrophils independently from their cell count in the circulation.

Example 4. A Phase 2a, Randomised, Double-Blind, Placebo-Controlled Study of Compound 1 in Adult Patients with Sickle Cell Anaemia (SCA)

Objectives

Primary Objectives: To assess the safety and tolerability of Compound 1 in adult patients with sickle cell anemia (SCA), defined as homozygous sickle haemoglobin (HbSS) or sickle-$\beta^0$ thalassemia, who are not receiving hydroxyurea (HU) and in adult SCA patients who are receiving a stable dose of HU.

Secondary Objectives: To characterize the pharmacokinetic (PK) profile of Compound 1 in adult patients with SCA who are/are not receiving a stable dose of HU; to characterize the PK profile of HU in adult patients with SCA before and after receiving Compound 1 to determine if there is a clinically relevant PK interaction.

Exploratory Objectives: To assess the pharmacodynamic (PD) effects of Compound 1 in adult patients with SCA who are/are not receiving stable HU; to assess the potential efficacy of Compound 1 on SCA-related clinical outcome measures in adult patients with SCA who are/are not receiving stable HU.

Methodology

This is a randomized, double-blind, placebo-controlled study to evaluate the safety, tolerability, PK, and exploratory PD and clinical outcomes of the phosphodiesterase 9 (PDE9) inhibitor, Compound 1, administered once daily for 16 to 24 weeks in 2 populations of patients with SCA: those who are not receiving HU (Population A) and those who are currently receiving a stable dose of HU according to standard of care (Population B). Up to approximately 36 patients are enrolled in Population A and 18 patients are enrolled in Population B.

Population A: Following a Screening period of up to 4 weeks, eligible patients in Population A (i.e., those not receiving HU) receive either Compound 1 or placebo for a total of 24 weeks. On Day 1, patients are randomized 1:1:1 to receive oral Compound 1 30 mg, 50 mg, Compound 1 100 mg, or placebo daily for the first 12 weeks; for the second 12 weeks (Weeks 13-24), each patient's dose may be doubled (i.e., from 50 mg to 100 mg; from 100 mg to 200 mg; or placebo). (Note because placebo and all dose levels of Compound 1 are the same in appearance, dose escalation does not affect study medication blinding). Throughout the study, all available clinical data are reviewed approximately every 2 weeks, and dose escalation occurs on an individual patient basis on Day 85 only if approved based upon review of each patient's individual clinical safety data.

Population B: Following a Screening period of up to 4 weeks, eligible patients in Population B (i.e., those receiving stable HU) enter a lead-in period and have blood samples drawn to characterize the PK profile of the patient's prescribed dose of HU in the absence of Compound 1 (i.e., to characterize the patient's baseline HU PK profile). Two full baseline HU PK profiles (with blood samples drawn over a 10-hour period at least 48 hours apart) are determined.

Compound 1 dosing in Population B do not begin until at least 4 weeks of safety data from 6 patients in Population A have been reviewed and determined that it is safe and appropriate to begin dosing in Population B. Following approval to initiate dosing in Population B and once the baseline HU PK blood draws are complete, patients are randomized 2:1 on Day 1 to receive oral Compound 1 30 mg, 50 mg or placebo for 16 weeks. For the first 4 weeks (Weeks 1-4), patients receive study medication according to their randomized treatment assignment; for the following 12 weeks (Weeks 5-16), each patient's dose may be doubled (e.g., from 50 mg to 100 mg; or placebo). As in Population A, dose escalation occurs on Day 29 only if approved based upon review of each patient's individual clinical safety data.

Study Design Rationale

This is the first study in a patient population (patients with SCA), and as such, is designed to examine the safety, tolerability, and PK, as well as the potential PD effects and clinical efficacy, of Compound 1 across a range of doses in adult patients with SCA. Given the possibility that Compound 1, if approved, could be administered as a single agent or co-administered with HU, the effects of Compound 1 are evaluated in SCA patients who are not receiving HU or any other treatment known to modulate HbF levels (Population A) as well as in those who are currently receiving a stable dose of HU (Population B).

Available nonclinical and healthy volunteer clinical data suggest that Compound 1 is safe and well tolerated at once daily doses of 30 50, 100, and 200 mg and that a potentially clinical beneficial PD effect is likely to be observed when a dose of at least 100 mg is administered for at least 24 weeks. Therefore, Population A is designed to explore the PD dose response in patients as well as the tolerability of the 200 mg dose level in sickle cell patients who have tolerated the 100 mg dose well.

Results from Population B are intended to provide information on Compound 1 when administered concomitantly with HU, both of which increase HbF levels through alternative biochemical pathways that increase intracellular cGMP. Because there are no clinical data to support administration of Compound 1 concomitantly with HU, patients in Population B initiate Compound 1 dosing at the low dose (30 mg or 50 mg) used in Population A and only escalate to the 100 mg dose if the 50 mg dose has been safe and tolerated for 4 weeks. In addition, although available nonclinical data do not suggest that concomitant administration of HU with Compound 1 would increase Compound 1 exposure, dosing in Population B does not initiate until 4 weeks of safety data are available from Population A in 2 patients each at 30 mg or 50 mg (starting dose in Population B) and at 100 mg (2× the starting dose) as well as placebo.

Diagnosis and Main Criteria for Inclusion

Inclusion Criteria

Each patient must meet all of the following criteria to be enrolled in the study: 1. Male or female ≥18 or ≤50 years of age. 2. Confirmed diagnosis of SCA (HbSS or sickle-β0 thalassemia). Note, if not already documented in the patient's record, the diagnosis of SCA must be confirmed via electrophoresis, HPLC, and/or genotyping. 3. Use of HU: For patients in the Population A: Have not received HU within 90 days prior to Screening and are not planning to take HU within the next 6 months. For patients in Population B: Have received HU for at least 6 months, have been on a stable dose for at least 60 days prior to Screening, and are not planning to change the dose level, dose regimen, or discontinue HU within the next 6 months. 4. Female patients must not be pregnant and be highly unlikely to become pregnant. Male patients must be unlikely to impregnate a partner.

Exclusion Criteria

Patients who meet any of the following criteria are excluded from the study: 1. Total Hb at Screening >11.0 g/dL or <6 g/dL. 2. Reticulocyte count <100×109/L. 3. >3 hospitalizations (for at least 24 hours) for vaso-occlusive crises (VOC), including acute chest syndrome (ACS) and priapism, within the prior year. 4. Receiving chronic outpatient opioid treatment (equivalent to ≥10 mg oral morphine daily) for any reason other than avascular necrosis (AVN). Note: chronic treatment is defined as continuous daily opioid use for ≥8 weeks. 5. Blood transfusion or donation of blood or any blood product within 60 days of Day 1 or on chronic transfusion therapy regimen. 6. Positive for human immunodeficiency virus (HIV), hepatitis C (HCV) antibodies (unless the patient has successfully completed drug therapy that results in cure/clearance of HCV), and hepatitis B surface antigen (HBsAg). 7. For female patients of childbearing potential, a positive serum human chorionic gonadotropin (hCG) test (Screening) or a positive urine hCG test on Day 1. 8. Estimated glomerular filtration rate (eGFR) <50 mL/min as calculated by the equation from the Modification of Diet in Renal Disease (MDRD) Study using creatinine, age, sex, and ethnicity. 9. Alanine aminotransferase (ALT) or aspartate aminotransferase (AST) >3× the upper limit of normal (ULN). 10. Body Mass Index (BMI) <17.5 or >35 kg/m2; a total body weight <50 kg. 11. Use of PDE5 inhibitors (including but not limited to sildenafil, tadalafil, vardenafil) within 7 days prior to the first dose of study drug, or planning to use any time during study. 12. A history of drug or alcohol abuse as judged by the investigator within the past 1 year, or a positive alcohol (breathalyzer) test (Screening or Day −1). 13. A cancer that has not been in complete remission for at least 5 years. Patients with squamous cell or basal cell carcinoma of the skin, localised cervical cancer, or localised prostate cancer are eligible if, in the opinion of the investigator, the condition has been adequately diagnosed, and is determined to be clinically in remission, and the patient's participation in the study would not represent a safety concern. 14. A history of a clinically significant allergic reaction or hypersensitivity, as judged by the investigator, to any drug or any component of the study drug formulations used in the study. 15. On ECG, a corrected QT interval, Fridericia's formula (QTcF) >450 ms in men and >470 ms in women or the presence of clinically significant abnormalities as determined by the investigator. 16. A history of major surgery within 4 weeks or minor surgery within 2 weeks of Day 1. 17. Any flu-like syndrome or other respiratory infection within 2 weeks of Day 1 or vaccination with attenuated live virus within 4 weeks of Day 1. 18. Participation in an investigational drug or device study within 30 days prior to Day 1. 19. Use within 30 days prior to Day 1, or planning to use during the study, of any drugs or substances that are known to strongly inhibit or induce cytochrome P450 enzymes (CYPs), including but not limited to cimetidine, cyclosporine, erythromycin, omeprazole, rifampin, ritonavir, and St. John's wort. If there is any question as to whether a substance is permitted, please review the product labelling (if applicable) and consult the Sponsor. 20. Consumption of grapefruit, grapefruit juice, or grapefruit products within 24 hours prior to Day 1 or planning to consume grapefruit products during the study. 21. Use within 30 days prior to Day 1, or planning to use during the study, of any CYP3A sensitive substrates, (excluding opioids), including but not limited to alfentanil, avanafil, budesonide, buspirone, conivaptan, darifenacin, darunavir, dasatinib, dronedarone, ebastine, eletriptan, eplerenone, everolimus, felodipine, ibrutinib, indinavir, lomitapide, lurasidone, maraviroc, midazolam, naloxegol, nisoldipine, quetiapine, saquinavir, sirolimus, tacrolimus, ticagrelor, tipranavir, tolvaptan, triazolam. 22. Use within 30 days prior to Day 1, or planning to use during the study, of any drugs or substances known to be significant substrates or inhibitors of P-glycoprotein (P-gp), including but not limited to cyclosporine, lovastatin, propranolol, quinidine, and simvastatin. If there is any question as to whether a substance is permitted, please review the product labelling (if applicable) and consult the Sponsor. 23. Other prior or ongoing medical condition, physical findings, or laboratory abnormality that, in the investigator's opinion, could adversely affect the safety of the patient, make it unlikely that the course of treatment or follow-up would be completed, or impair the assessment of study results.

Investigational Product, Dosage and Mode of Administration

Compound 1 is supplied as 50, 100 or 200 mg white tablets and is administered orally with food. The different doses of Compound 1 are visually identical in tablet form.

Reference Therapy, Dosage and Mode of Administration

Placebo consists of tablets containing matrix absent Compound 1 and is identical in appearance to the Compound 1 tablets. Placebo is administered orally with food.

Duration of Treatment

The total duration of the study is approximately 32 weeks for Population A, including a Screening period of up to 4 weeks, a treatment period of 24 weeks, and a 4-week follow-up assessment after the last dose of study drug is administered.

The total duration of the study is approximately 32 weeks for Population B, including a Screening period of up to 4 weeks, a lead-in period of approximately 8 weeks, a treatment period of 16 weeks, and a 4-week follow-up assessment after the last dose of study drug is administered.

Endpoints

The endpoints for Populations A and B are the same except where noted otherwise.

Primary Endpoints: Compound 1 safety and tolerability as measured by: Incidence and severity of adverse events (AEs) and serious adverse events (SAEs); Change from baseline in 12-lead electrocardiogram (ECG) parameters, clinical laboratory tests (chemistry, hematology, coagulation, urine), and vital signs; Physical examination findings.

Secondary Endpoints: The plasma PK profile of Compound 1 after oral administration to adult patients with SCA (Populations A and B); The plasma PK profile of HU before and after oral administration of Compound 1 to adult patients with SCA (Population B only).

Exploratory Endpoints: Compound 1 PD as measured by the following (additional exploratory biomarkers may also be tested): Total haemoglobin (Hb) levels; HbF value (%); % F cells; Indices of red cell haemolysis (unconjugated bilirubin, reticulocyte count, lactase dehydrogenase [LDH], and haptoglobin levels); Soluble E-selectin (sE-Sel), Soluble P-selectin (sP-Sel) and soluble intercellular adhesion molecule 1 (sICAM-1); High sensitivity-C reactive protein (hs-CRP). Compound 1 clinical outcomes as measured by pain-related measures (frequency, severity, and duration of pain; impact of pain/fatigue on work/school and on activities of daily living; need for/use of pain medication; SCA-related events requiring professional medical or health care, including events requiring hospitalization or therapies, such as transfusions) and in the physical, social, and emotional impact of SCA as measured by the Adult Sickle Cell Quality-of-Life Measurement Information System (ASCQ-Me).

In addition, a separate blood sample is collected for confirmation of diagnosis by electrophoresis, high performance liquid chromatography (HPLC) and/or DNA sequencing (as needed) as well as for possible pharmacogenomic analyses of genes that may affect treatment response (including but not limited to alpha globin and BCL11A).

What is claimed is:

1. An oral tablet composition, comprising:
    50 mg 6-[(3S,4S)-4-methyl-1-(pyrimidin-2-ylmethyl) pyrrolidin-3-yl]-3-tetrahydropyran-4-yl-7H-imidazo[1,5-a]pyrazin-8-one (Compound 1),
    about 20%, about 30%, or about 40% by weight microcrystalline cellulose (MCC),
    about 1% by weight colloidal silicon dioxide, and
    about 0.8% by weight magnesium stearate.

2. The oral tablet composition of claim 1, comprising from 20% to 40% by weight Compound 1.

3. The oral tablet composition of claim 1, further comprising one or more solid carriers.

4. The oral tablet composition of claim 3, wherein the one or more solid carriers comprise lactose.

5. The oral tablet composition of claim 1, wherein Compound 1 is present as a monohydrate.

6. The oral tablet composition of claim 1, wherein Compound 1 is present as a monohydrate polymorph.

7. An oral tablet composition, comprising:
    50 mg 6-[(3S,4S)-4-methyl-1-(pyrimidin-2-ylmethyl) pyrrolidin-3-yl]-3-tetrahydropyran-4-yl-7H-imidazo[1,5-a]pyrazin-8-one (Compound 1),
    about 20% or about 30% by weight microcrystalline cellulose (MCC),
    about 1% by weight colloidal silicon dioxide,
    about 0.8% by weight magnesium stearate, and
    one or more solid carriers comprising lactose.

* * * * *